(12) United States Patent
Klein et al.

(10) Patent No.: US 9,384,925 B2
(45) Date of Patent: Jul. 5, 2016

(54) STERILE DISPOSABLE REMOTE PNEUMATIC ACTUATORS

(71) Applicant: HK Surgical, Inc., San Clemente, CA (US)

(72) Inventors: Jeffrey Alan Klein, San Juan Capistrano, CA (US); Randall Welch, Mission Viejo, CA (US)

(73) Assignee: HK SURGICAL, INC., San Clemente, CA (US)

( * ) Notice: Subject to any disclaimer, the term of this patent is extended or adjusted under 35 U.S.C. 154(b) by 10 days.

(21) Appl. No.: 13/965,853

(22) Filed: Aug. 13, 2013

(65) Prior Publication Data

US 2013/0331776 A1     Dec. 12, 2013

Related U.S. Application Data

(63) Continuation of application No. 13/009,808, filed on Jan. 19, 2011, now abandoned.

(60) Provisional application No. 61/296,374, filed on Jan. 19, 2010.

(51) Int. Cl.
*H01H 35/32*     (2006.01)
*A61M 3/02*      (2006.01)
*A61B 18/20*     (2006.01)
(Continued)

(52) U.S. Cl.
CPC ............... *H01H 35/32* (2013.01); *A61B 18/20* (2013.01); *A61M 1/0039* (2013.01); *A61M 1/0064* (2013.01); *A61M 3/0258* (2013.01);
(Continued)

(58) Field of Classification Search
CPC ............ A61M 1/0039; A61M 1/0041; A61M 1/0058; A61M 1/0064; H01H 35/32; H01H 35/34
USPC ............ 604/35, 140, 141, 143, 144, 146, 153
See application file for complete search history.

(56) References Cited

U.S. PATENT DOCUMENTS 3,494,363 A     2/1970 Jackson
3,873,790 A     3/1975 Coons
(Continued)

FOREIGN PATENT DOCUMENTS

DE          93 08 695 U1    10/1993
WO      WO 2011/066577 A1    6/2011

OTHER PUBLICATIONS

International Search Report in corresponding International Application No. PCT/US2011/021764, dated May 25, 2011.

*Primary Examiner* — Kami A Bosworth
*Assistant Examiner* — Nilay Shah
(74) *Attorney, Agent, or Firm* — Knobbe, Martens, Olson & Bear, LLP

(57) ABSTRACT

The various embodiments of the present invention relate to remote pneumatic (bellows-action) actuators for switching applications, which are preferably sterile and/or disposable. When compressed, the bellows-action actuator provides a pulse of air pressure sufficient to actuate a remotely-located pneumatic switch configured to turn on/off an electrical, mechanical or optical device. The pulse of air pressure is propagated along a non-conducting tube, thereby substantially reducing the risk of e.g., electric shock or $O_2$ ignition/combustion associated with conventional electric switches in wet, hazardous or medical environments.

8 Claims, 19 Drawing Sheets

(51) Int. Cl.
*A61M 5/172* (2006.01)
*A61M 1/00* (2006.01)

(52) U.S. Cl.
CPC ............ *A61M3/0283* (2013.01); *A61M 5/172* (2013.01); *A61M 1/0041* (2013.01); *A61M 1/0058* (2013.01)

(56) References Cited

U.S. PATENT DOCUMENTS

| | | |
|---|---|---|
| 3,885,267 A | 5/1975 | Maurer et al. |
| 3,918,453 A | 11/1975 | Leonard |
| 4,314,560 A | 2/1982 | Helfgott et al. |
| 4,639,156 A | 1/1987 | Stern et al. |
| 5,059,182 A * | 10/1991 | Laing ............................ 604/142 |
| 5,090,963 A * | 2/1992 | Gross et al. .................... 604/132 |
| 5,139,357 A | 8/1992 | Reents |
| 5,399,166 A * | 3/1995 | Laing ............................ 604/146 |
| 5,484,402 A | 1/1996 | Saravia et al. |
| 5,542,905 A * | 8/1996 | Nussenbaum ................ 600/197 |
| 5,662,605 A | 9/1997 | Hurwitz |
| 5,733,117 A | 3/1998 | Coss et al. |
| 6,213,970 B1 | 4/2001 | Nelson et al. |
| 6,508,823 B1 | 1/2003 | Gonon |
| 6,623,445 B1 | 9/2003 | Nelson et al. |
| 6,652,488 B1 | 11/2003 | Keast et al. |
| 2006/0255063 A1* | 11/2006 | Gallnbock ....................... 222/95 |
| 2009/0036874 A1* | 2/2009 | Horowitz et al. ............. 604/544 |

* cited by examiner

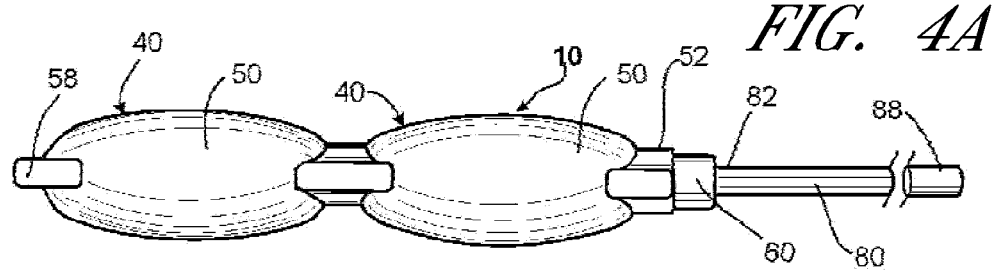
*FIG. 4A*
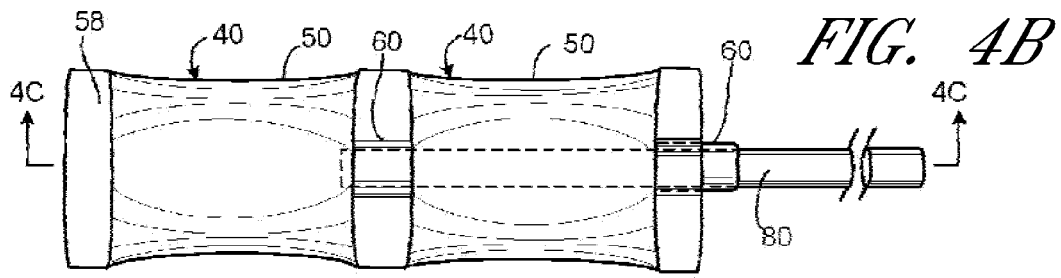
*FIG. 4B*
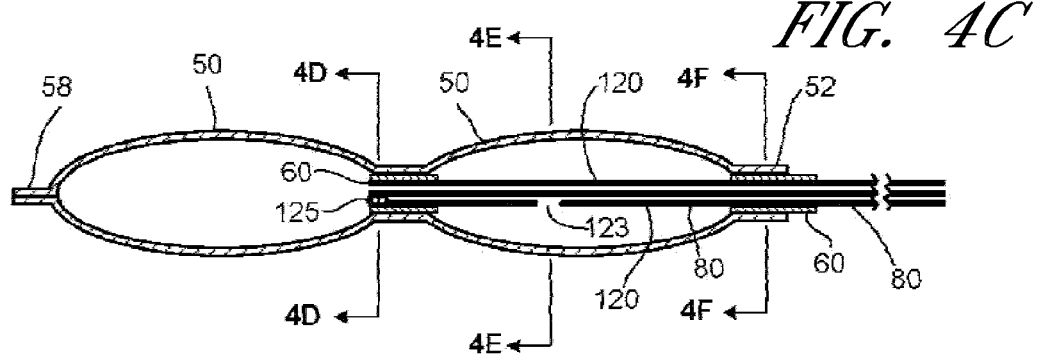
*FIG. 4C*
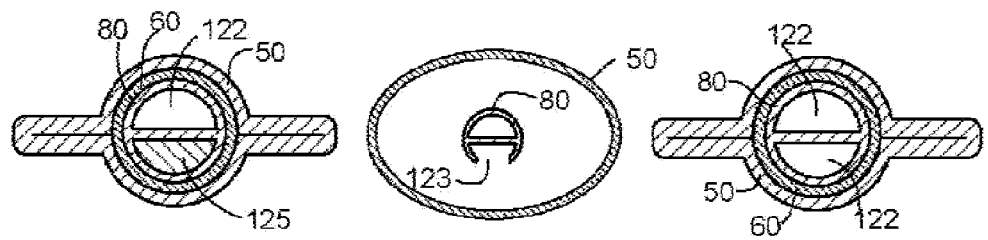
*FIG. 4D*   *FIG. 4E*   *FIG. 4F*

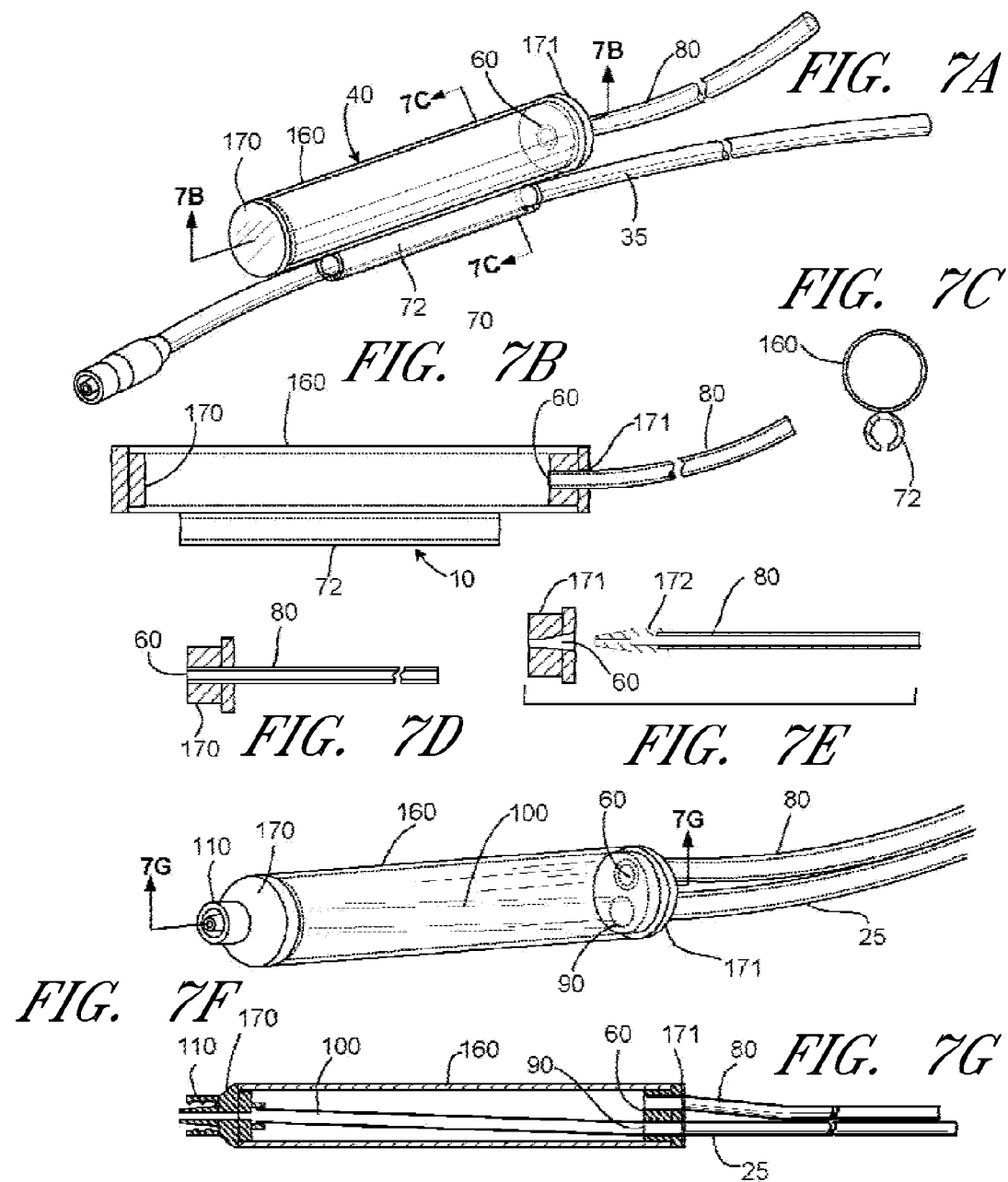

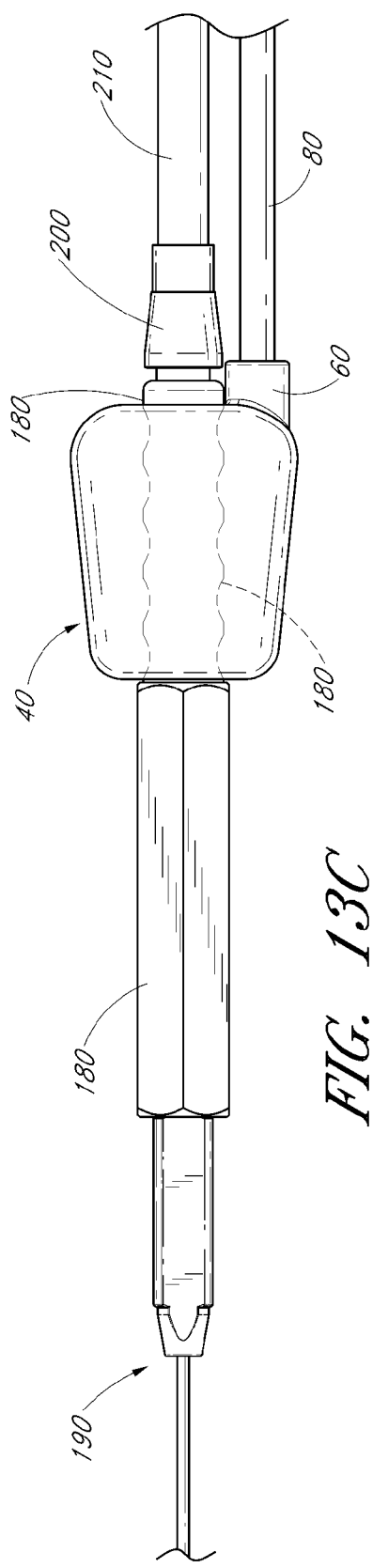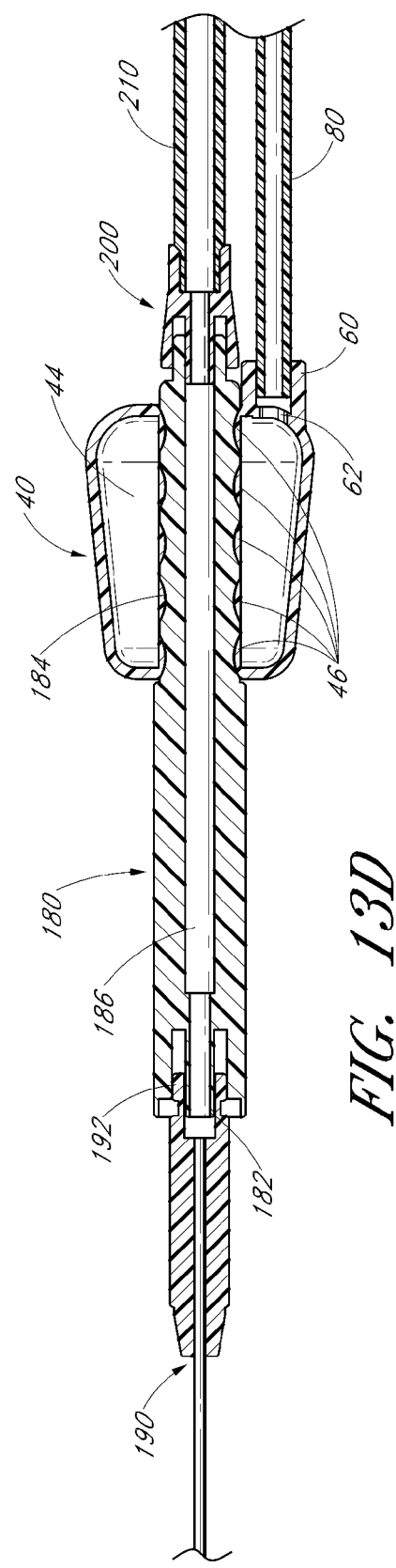

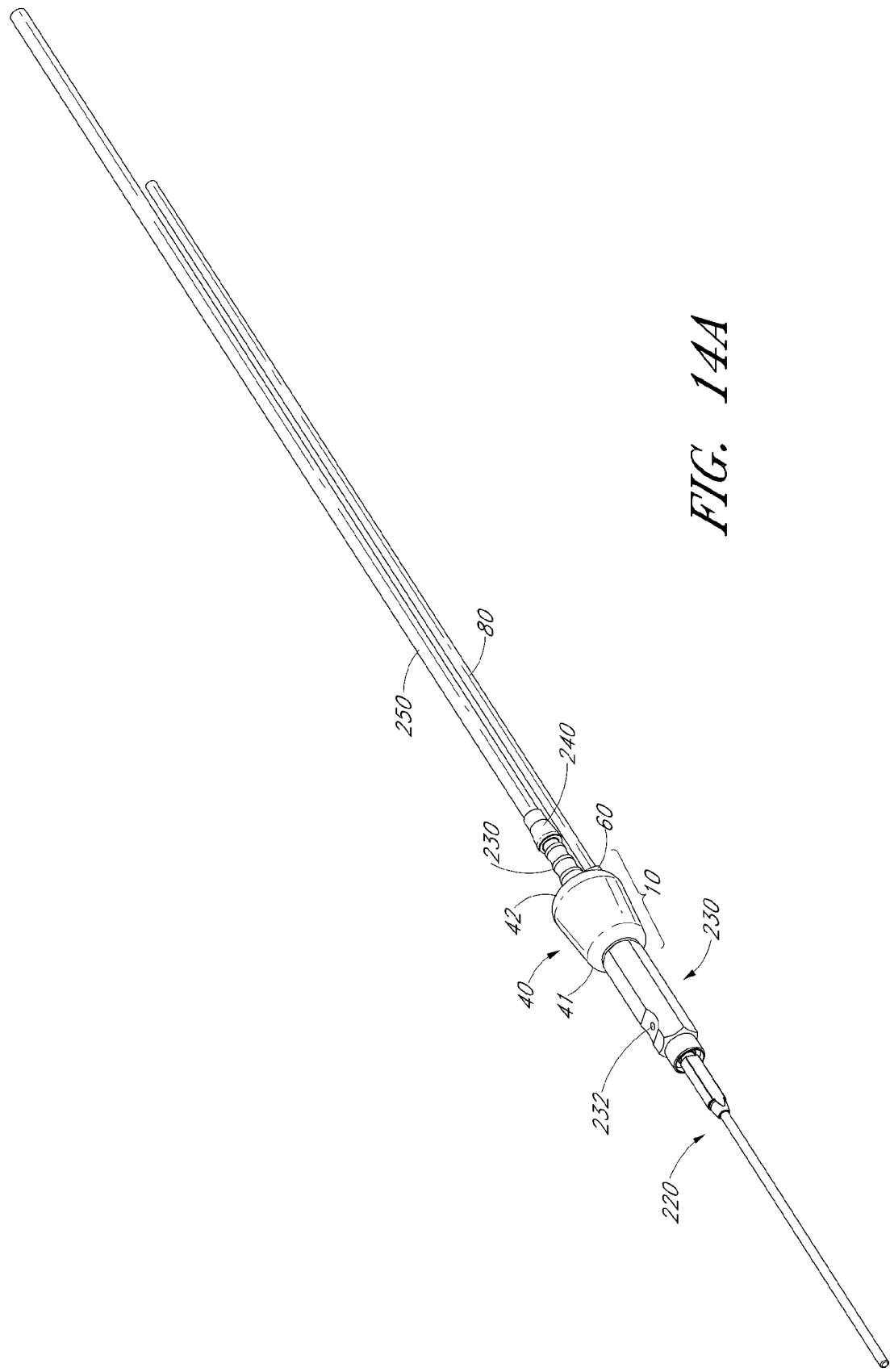

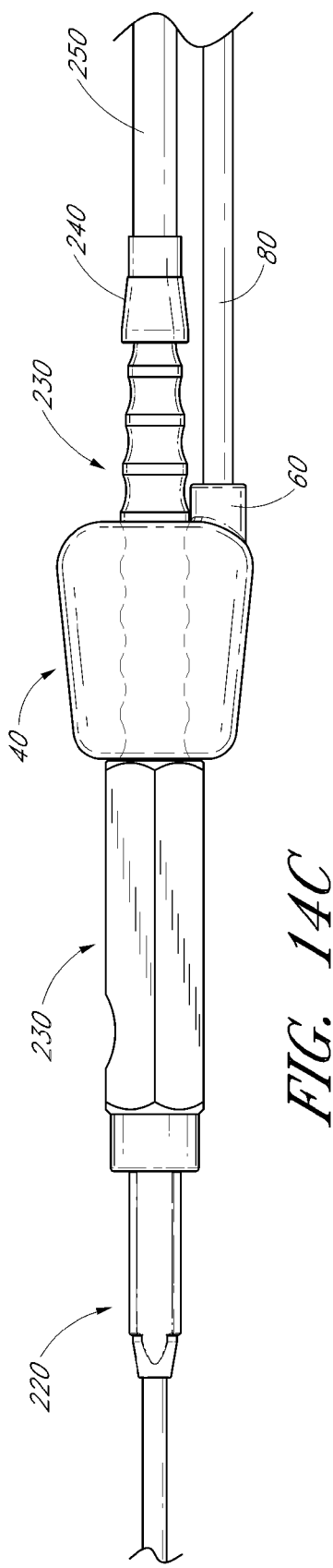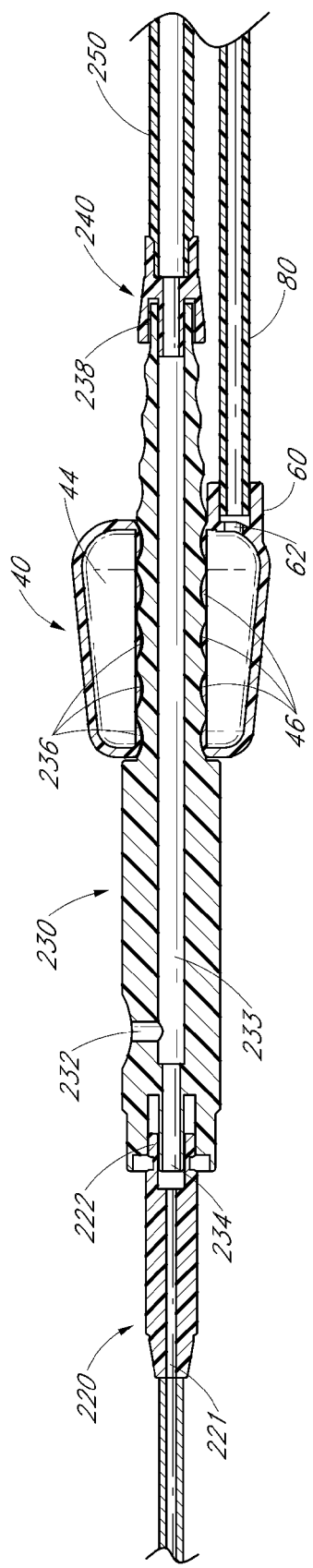

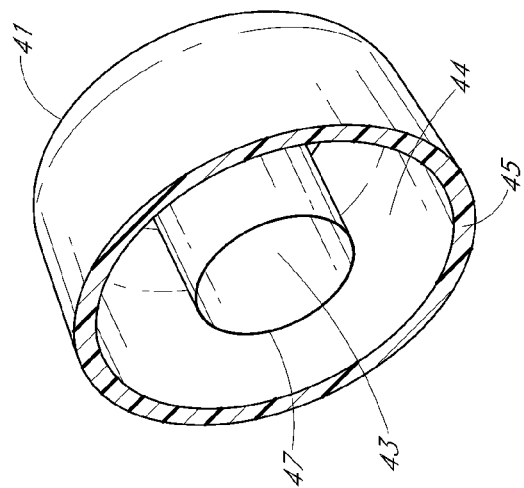
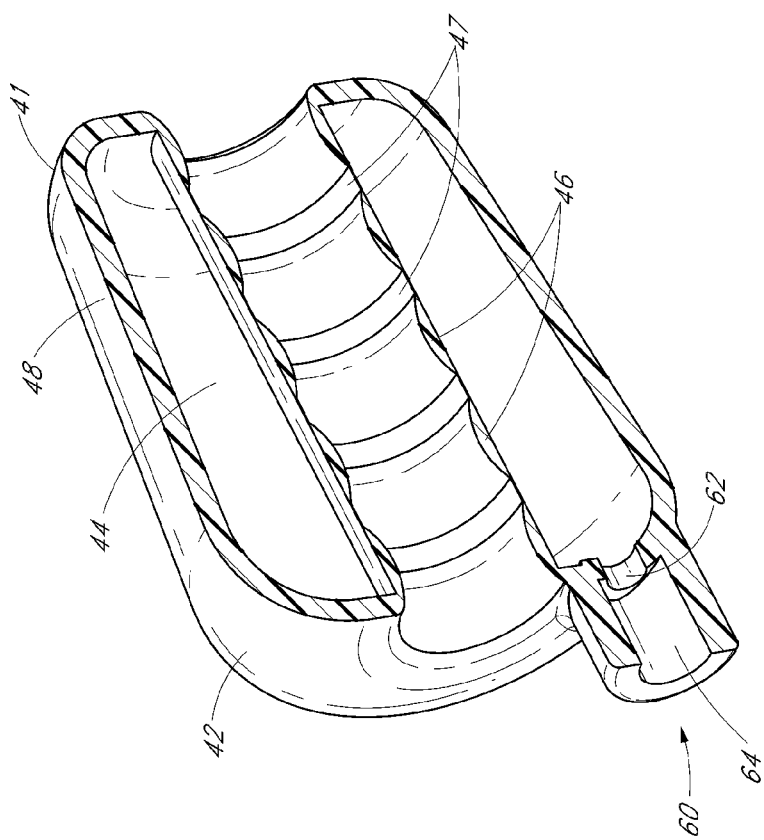
FIG. 15F
FIG. 15E

STERILE DISPOSABLE REMOTE PNEUMATIC ACTUATORS

RELATED APPLICATIONS

This application is a continuation of U.S. application Ser. No. 13/009,808, filed Jan. 19, 2011, which claims priority to U.S. Provisional Application No. 61/296,374 filed on Jan. 19, 2010, the entire contents of which are incorporated herein by reference.

BACKGROUND

1. Field

Aspects of the invention relate generally to pneumatic actuators or switches. More particularly, bellows-action, remote pneumatic actuators are disclosed, wherein such actuators are preferably sterile or sterilizable, and configured for one-time use.

2. Description of the Related Art

There are many examples of electric powered devices that require a remotely controlled on-off switch. For example, with a ceiling light bulb, a remote on-off switch facilitates efficient utilization. A more specific example is an electric powered medical device such as a peristaltic infiltration pump used by a surgeon.

When using such a pump, a surgeon wears sterile gloves and holds a sterile infiltration cannula connected to plastic pump-tubing, similar to intravenous tubing, which in turn is connected to a reservoir of sterile solution. The clinical goal is to inject a controlled volume of solution through the infiltration cannula and into a patient's subdermal or deep tissues.

In this setting, the reservoir of sterile solution and the peristaltic pump, the outer surfaces of which are not sterile, are positioned remotely from the aseptically prepared and sterilely draped surgical site. The sterile solution is transported via a peristaltic roller pump tubing set that connects the reservoir to the infiltration cannula. The patient end of this tubing set, as well as the infiltration cannula held by the surgeon, come into contact with the surgical site and must remain sterile. The other end of the tubing which is connected to the reservoir and passes through the peristaltic pump is not intended to have a sterile external surface.

In order to actuate and operate the pump with finesse during surgery, the surgeon must have easy access to a remotely controlled on-off switch. During surgery the surgeon wears gloves which must remain sterile throughout the duration of the procedure. Thus any surgeon-controlled on-off switch is typically either a sterile hand-held switch or a non-sterile foot-pedal switch.

When a surgical procedure requires two or more remotely controlled electrically powered devices, the surgeon must be in control of two or more on-off switches. For example, the surgery might require the use of multiple electrically powered devices such as, for example, a peristaltic infusion pump, an electric suction-vacuum pump, a laser device or an electric cautery device. In order to avoid the risks of an electric shock to the patient or the surgeon, it is desirable that the on-off switches that control electrically powered surgical devices be connected to the surgical devices by materials that do not conduct an electric current.

One option is a disposable battery-operated hand-control which utilizes radio frequency or infra-red frequency electromagnetic waves. However, disposable battery-operated hand-controls are relatively expensive and require battery disposal protocols. A battery powered remote-controlled disposable pump connected by copper wires to a handheld switch also has the disadvantage of being relatively expensive. See e.g., the StrykeFlow2 (San Jose, Calif. 95138), a battery operated suction and irrigation system with a disposable hand piece and built-in pump motor; See also U.S. Pat. Nos. 5,484,402; 6,213,970; 6,623,445; and 6,652,488; incorporated herein in their entireties by reference thereto.

Another option is the use of a foot pedal switch. The advantage of a foot pedal switch is that it need not be sterile and can be reused many times. However, there are several disadvantages of a foot switch. Firstly, foot-eye coordination is not as precise as hand-eye coordination. Second, the surgeon must occasionally remove his/her attention and visual focus from the patient and the surgical field in order to visually locate the foot pedal. Third, when there are two or more foot pedals, the surgeon's attention and vision must frequently be diverted toward the floor in order to be certain that the surgeon's foot is being placed on the correct foot pedal switch. Fourth, foot pedals, wires, cords, and tubes which are located on a surgical operating room floor are easily contaminated by blood-born pathogens and therefore must be washed or cleaned after each surgery, which is an expensive and labor intensive process. Fifth, in situations where there are multiple pedals and tubes or wires on the operating room floor, there is a serious risk of tripping on the tangled cords with subsequent injury to staff or the patient.

In order to avoid confusion and possible mistakes, the multiple foot switches must each have a distinct and easily recognized appearance. Such a solution is problematic in any clinical situation which requires a darkened or low-light operating room environment. Furthermore, the risk of inadvertently stepping on the wrong foot switch or tripping on a tangle of tubing on the floor cannot be entirely eliminated. The use of a foot-switch necessarily entails some constraint on a surgeon's ability to choose an optimal body posture and foot position. A challenging or difficult surgical maneuver often requires that the surgeon be able to maintain a comfortable and stable body position with weight appropriately distributed on each foot.

Another option for an on-off switching apparatus that does not conduct an electric current is a combination of a pneumatic bellows-action hand-control connected by means of plastic tubing to a pneumatic diaphragm-triggered electric switch located within the remote electrically powered surgical device. Such a switching means can be either reusable or disposable.

Reusable, pneumatic, bellows-action hand-controls are not generally designed for use in a sterile setting. A reusable, hand-control on-off switch for a surgical device must be sterilizable, e.g., by heat sterilization in a steam autoclave. Such design requirements result in a device that is expensive to manufacture. Furthermore, reusable bellows-action hand-control switches may be prone to increased risk of transmitting blood borne pathogens.

Existing bellows-action hand-controls are intended for reusable use in non-medical industries. Modifying such reusable hand-control switches for a specific clinical situation is often prohibitively expensive, and the switch may be awkward to use. At present the only commercially available pneumatic bellows-action hand-control devises are rather cumbersome, not easily sterilized and expensive.

Remote control on-off switches are known in the art. Such switches are designed to provide convenient activation of a remote electrical device. However, despite the development of many approaches to such switches, these approaches often have significant drawbacks.

Accordingly, there is a need for a pneumatic, e.g., bellows-action, hand-held remote actuator, that is safe (e.g., does not conduct an electrical current), inexpensive, light-weight, small, reliable and with few moving parts, that can be easily coupled to one or more surgical devices. Preferably, the remote actuator is sterile or sterilizable and disposable.

SUMMARY OF THE INVENTION

A remote actuator for a medical device that comprises a pneumatic switch, a medical tube and a treatment member is disclosed. The remote actuator comprises: a bellows having a pneumatic port and a means for reversibly attaching the remote actuator to either the medical tube or the treatment member; and an actuating tube with proximal and distal ends, wherein the proximal end is pneumatically coupled to the pneumatic port and the distal end is configured to pneumatically couple to the pneumatic switch on the medical device, such that application of pressure to the bellows generates sufficient air pressure to actuate the pneumatic switch.

In one embodiment, the treatment member of the remote actuator comprises a cannula for fluid infiltration, infusion or suction. In some embodiments, at least the bellows of the remote actuator is sterile. In one embodiment, the remote actuator is disposable and configured for a single use.

The remote actuator may further comprise a salable package comprising an outer wrapper defining a sealed and sterile interior, wherein the remote actuator is located within the sealed and sterile interior.

One embodiment relates to a handle for the treatment member, wherein the handle is provided with a remote actuator. In several embodiments the remote actuator is an integrated member of the handle. In some embodiments the handle is reusable. In other embodiments the handle is configured for single use.

The handle may further comprise a salable package comprising an outer wrapper defining a sealed and sterile interior, wherein the handle is located within the sealed and sterile interior.

One embodiment relates to a remote actuator comprising a bellows, wherein the bellows comprises a lumen which is pneumatically coupled to a pneumatic port. In some embodiments the remote actuator further comprises an actuator tube which pneumatically couples the bellows' lumen to a pneumatic switch of a medical device. In several embodiments the bellows comprises a channel that is pneumatically sealed from the bellows lumen. In several embodiments the bellows may be reversibly affixed to the handle of a treatment member by passing a segment of the handle through the channel. In some embodiments the bellows is reusable. In other embodiments the bellows is disposable and configured for single use.

The remote actuator may further comprise a salable package comprising an outer wrapper defining a sealed and sterile interior, wherein the bellows and optionally one or more of an actuating tube, a handle for a treatment member and a treatment member are located within the sealed and sterile interior.

In another embodiment, a remote actuator for a medical device that comprises a pneumatic switch, a medical tube and a treatment member is disclosed. The remote actuator comprises: a bellows comprising a pneumatic port and first and second fluid ports and an internal conduit therebetween, wherein the fluid ports and internal conduit are configured to allow fluid coupling of the medical tube and the treatment member; and an actuating tube pneumatically coupled to the pneumatic port of the bellows and configured to allow pneumatic coupling to the pneumatic switch on the medical device, such that application of pressure to the bellows generates sufficient air pressure to actuate the pneumatic switch.

In some embodiments, the treatment member comprises an infiltration, infusion or suction cannula. In some embodiments, the treatment member comprises a laser. At least the bellows of the remote actuator is preferably sterile. In some embodiments, the remote actuator is configured for a single use.

In a variation, the internal conduit comprises first and second lumens, wherein the first lumen is fluidly coupled to the medical tube and the treatment member, and wherein the second lumen comprises the pneumatic port within the bellows, and is pneumatically coupled to the actuating tube.

In one embodiment, the remote actuator further comprises a salable package comprising an outer wrapper defining a sealed and sterile interior, wherein the remote actuator is located within the sealed and sterile interior.

In accordance with another embodiment, a remote actuator for a surgical laser that comprises a pneumatic switch, a medical tube having an optical fiber laser therein, and a laser treatment cannula is disclosed. The remote actuator for the surgical laser comprises: a bellows comprising a pneumatic port and first and second laser ports and an internal conduit therebetween, wherein the laser ports and internal conduit are configured to allow the optical fiber laser to traverse the bellows and emerge from the laser treatment cannula; and an actuating tube pneumatically coupled to the pneumatic port of the bellows and configured to allow pneumatic coupling to the pneumatic switch on the surgical laser, such that application of pressure to the bellows generates sufficient air pressure to actuate the pneumatic switch.

The internal conduit may comprises first and second lumens, wherein the first lumen is coupled to the medical tube and the treatment cannula, and wherein the second lumen comprises the pneumatic port within the bellows, and is pneumatically coupled to the actuating tube.

In some embodiments, the remote actuator for the surgical laser further comprises a salable package comprising an outer wrapper defining a sealed and sterile interior, wherein the remote actuator is located within the sealed and sterile interior.

Some embodiments relate to multiple remote actuators for control of one or more surgical devices. In some embodiments each remote actuator comprises a pneumatic switch and a medical tube. In some embodiments a multiple remote actuator comprises: at least first and second bellows coupled together in series, each comprising a pneumatic port, wherein the coupled bellows further comprise at least first and second fluid ports and an internal conduit therebetween; and at least two actuating tubes pneumatically coupled to the pneumatic ports of each bellows, each actuating tube being configured to allow pneumatic coupling to the pneumatic switch on one of the surgical devices, such that application of pressure to a bellows generates sufficient air pressure to actuate the respective pneumatic switch.

In one embodiment, the one or more surgical devices comprise a fluid pumping device and a fluid suctioning device.

In some embodiments, the multiple remote actuator further comprises a salable package comprising an outer wrapper defining a sealed and sterile interior, wherein the multiple remote actuator is located within the sealed and sterile interior.

In a variation, the internal conduit comprises at least first and second lumens pneumatically coupled to the respective first and second pneumatic ports of the first and second bellows, and at least one additional lumen fluidly coupled to the fluid ports.

A system is disclosed in accordance with another embodiment. The system comprises: a medical device that comprises a pneumatic switch, a medical tube and a treatment member; and a remote actuator that comprises a bellows having an internal conduit therein, wherein the internal conduit comprises first and second lumens, wherein the first lumen is fluidly coupled to the medical tube and the treatment member, and wherein the second lumen comprises a port within the bellows, and is pneumatically coupled to an actuating tube which is pneumatically coupled to the pneumatic switch on the medical device, such that application of pressure to the bellows generates sufficient air pressure to actuate the pneumatic switch.

In one variation, the system further comprises a dual lumen tube that integrates the medical and actuating tubes within separate lumens for at least part of the distance between the medical device and the bellows.

In another variation, the system further comprises at least two medical devices and at least two remote actuators. In some embodiments, the at least two remote actuators are connected in series to facilitate single-handed control of the at least two medical devices.

In another variation to the system, the treatment member comprises an infiltration, infusion or suction cannula. Preferably, at least the bellows of the remote actuator is sterile. In some embodiments, the remote actuator is configured for a single use.

A system is disclosed in relation to another embodiment. The system comprises: a medical device that comprises a pneumatic switch, a medical tube, a handle and a treatment member; and a remote actuator that comprises a bellows configured such that the walls of the bellows form a channel which is pneumatically sealed from the bellow's lumen which is pneumatically coupled to an actuating tube which is pneumatically coupled to the pneumatic switch on the medical device, such that application of pressure to the bellows generates sufficient air pressure to actuate the pneumatic switch.

In one variation, the system further comprises a dual lumen tube that integrates the medical and actuating tubes within separate lumens for at least part of the distance between the medical device and the bellows.

In another variation, the system further comprises at least two medical devices and at least two remote actuators. In some embodiments, the at least two remote actuators are connected in series to facilitate single-handed control of the at least two medical devices.

In another variation to the system, the treatment member comprises an infiltration, infusion or suction cannula. Preferably, at least the bellows of the remote actuator is sterile. In some embodiments, the remote actuator is configured for a single use.

Other features and advantages of the embodiments will become apparent from the following more detailed description, taken in conjunction with the accompanying drawings.

BRIEF DESCRIPTION OF THE DRAWINGS

FIG. 3A shows a partially transparent top plan view of a remote actuator, illustrating an actuating tube and a fluid outlet port.

FIG. 3B shows a partially transparent view of an actuating tube, illustrating internal conduits.

FIG. 4A shows a side elevational view of a remote actuator, illustrating an actuating tube and two bellows.

FIG. 4B shows a partially transparent top plan view of a remote actuator, illustrating an actuating tube and two bellows.

FIG. 4C shows a cross section diagram showing an actuating tube and two bellows, taken generally along lines 4C-4C of FIG. 4B.

FIG. 4D shows a cross section diagram showing an occluder in a conduit of an actuating tube, taken generally along lines 4D-4D of FIG. 4C.

FIG. 4E shows a cross section diagram showing an actuating tube in a pouch, taken generally along lines 4E-4E of FIG. 4C.

FIG. 4F shows a cross section diagram showing an actuating tube in a pneumatic port, taken generally along lines 4F-4F of FIG. 4C.

FIG. 7A shows a partially transparent perspective view of a length of tubing, hermetically sealed end caps, a C-shaped resilient clamp, and a medical tube.

FIG. 7B shows a partially transparent side elevational view of a length of tubing, hermetically sealed end caps, and a C-shaped resilient clamp.

FIG. 7C shows a front elevational view of a length of tubing and a C-shaped resilient clamp.

FIG. 7D shows a side cross-section view of an actuating tube and a hermetically sealed end cap.

FIG. 7E shows a side cross-section view of an actuating tube and a hermetically sealed end cap with slip luer connectors.

FIG. 7F shows a partially transparent perspective view of a bellows consisting of a length of tubing, hermetically sealed end caps, an air conducting tube, a fluid outlet port, a fluid inlet port, and a fluid conduit.

FIG. 7G shows a partially transparent cross-section view of 7F, a length of tubing, hermetically sealed end caps, a fluid outlet port, a fluid inlet port, a fluid conduit, and a fluid supply tube.

FIG. 13C shows a partially transparent side elevational view of an infiltration cannula assembly.

FIG. 13D shows cross sectional diagram of an infiltration cannula assembly.

FIG. 14A shows a perspective view of an aspiration cannula assembly.

FIG. 14C shows a partially transparent side elevational view of an aspiration cannula assembly.

FIG. 14D shows cross sectional diagram of an aspiration cannula assembly.

FIG. 15E shows a cross section diagram of a second-end perspective view of a bellows, taken generally along lines 15E of FIG. 15B.

FIG. 15F shows a transverse cross section diagram of a second-end perspective view of a bellows, taken generally along lines 15F of FIG. 15B.

DETAILED DESCRIPTION

Figure 1A:
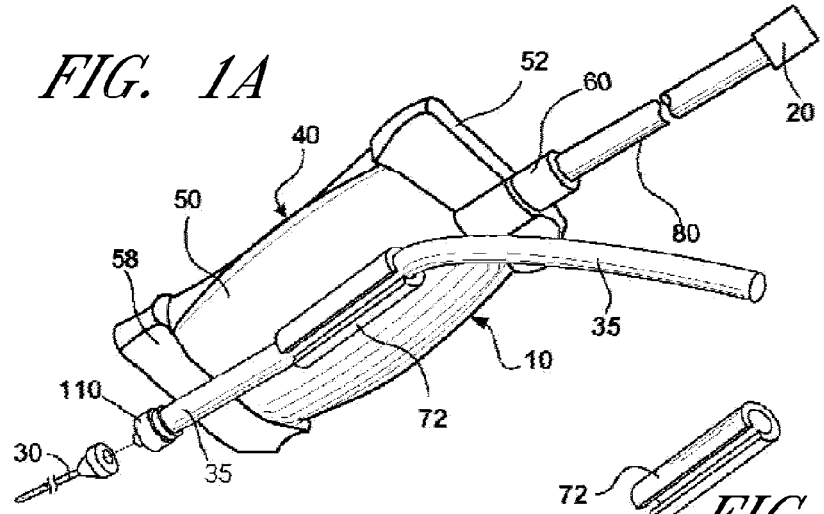
FIG. 1A shows a perspective view of a remote actuator.
Figures 1B, 1F:
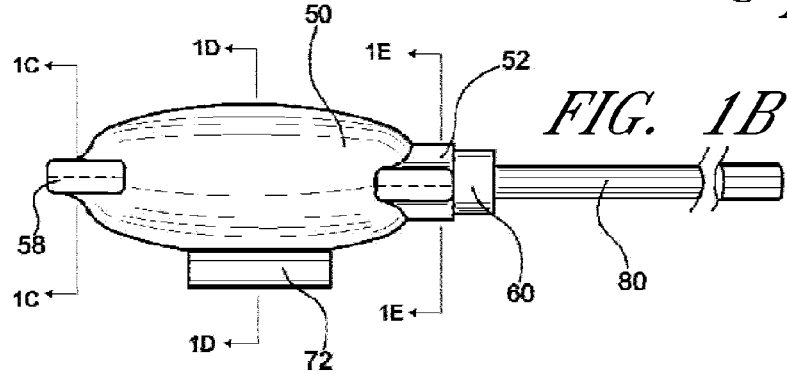
FIG. 1B shows a side elevational view of a remote actuator.
FIG. 1F shows a perspective view of a C-shaped resilient clamp.
Figure 1C:
FIG. 1C shows a cross section diagram showing a second end of a pneumatically sealed pouch, taken generally along lines 1C-1C of FIG. 1B.
Figure 1D:
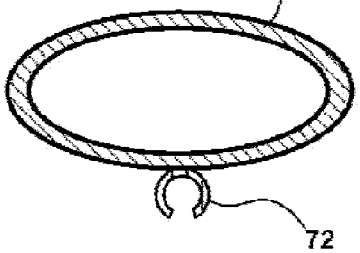
FIG. 1D shows a cross section diagram showing a part of a pneumatically sealed pouch, taken generally along lines 1D-1D of FIG. 1B.
Figure 1E:
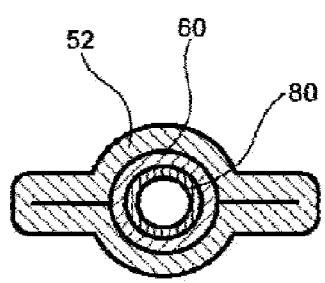
FIG. 1E shows a cross section diagram showing a part of a first end of a pneumatically sealed pouch, taken generally along lines 1E-1E of FIG. 1B.

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Some pneumatic and/or remote switching applications have been disclosed by others. For example, Coons (U.S. Pat. No. 3,873,790) and Maurer (U.S. Pat. No. 3,885,267), describe a household vacuum cleaner with a button/switch located on the handle of the vacuum hose, wherein the switch forms an integral part of the flexible hose. The pneumatic switch comprises an actuating piston that is spring-urged to place a cylinder in an expanded condition. The button is a functional piston which when depressed provides a pulse of air pressure to actuate the remote electric switch on the vacuum motor. The pneumatic pulse conduit tube that conducts the pulse of air that actuates the motor is longitudinally joined to the suction hose, which thereby prevents entanglement of the two tubes. This actuator-button has multiple moving parts rather than a simple air bladder.

Stern (U.S. Pat. No. 4,639,156) and Reents (U.S. Pat. No. 5,139,357) disclose a pneumatic actuator for an electrical switch in a portable painting apparatus. The Reents device comprises an actuator button that is integrated into the handle of the paint applicator or brush. The button is resilient, deformable and retained in a rigid base. When the button is depressed, a pulse of air pressure actuates an electric pump which delivers paint to the interior of the paint brush bristles. The button has a hole venting to ambient atmosphere. Thus this device is not isolated from the atmosphere, and therefore there is the potential for fluid to enter into the vent-hole. The button and handle are integral and specifically designed for industrial application.

Hurwitz (U.S. Pat. No. 5,662,605) discloses a hand-held device for irrigating external ear canal to remove waxy secretions. The device is connected to a distant open reservoir of tap water by a flexible hose. An electric pump delivers water to the hand piece. A remote control button is incorporated into the hand-piece held by the clinician. The on-off control button is connected to the pump by wires that conduct electricity. Electrically conducting wires are utilized to actuate an electric switch on the pump, rather than a pneumatic non-conducting switch. Thus, there is a potential for electric shock if there is a failure of the insulation on the wire connecting the hand piece and the pump.

Coss (U.S. Pat. No. 5,733,117) disclosed a water-flushing pump accessory to an air compressor driven dental drill, this hand-held device requires no remote hand-held control. The exhaust air pressure from the dental drill motor activates a pressure sensitive switch on the pump automatically when the dental drill is activated. This invention is intended to provide sterile water for irrigation of a surgical site via a distant peristaltic pump and reservoir of sterile water. However, actuation of the fluid pump as described by Coss is dependent upon actuation of the drill—there is no independent on/off switch for the pump.

The following explanation of terms is to provide an understanding of the usage and meaning of the terms. The explanations are a starting point for understanding these terms, but the terms are not necessarily limited to the following explanations. The terms may be further explained and understood from their usage in this specification and from the associated drawings.

Tumescent Related Terms

Tumescent, tumescence: Swollen and firm, tumid.

Tumescent technique, tumescent infiltration: The tumescent technique is a method of delivering large volumes of a dilute solution of a medication into subcutaneous tissue or deep parenchymal tissue. In the case of subcutaneous tissue, the solution may be infiltrated together with a vasoconstrictor, e.g., dilute epinephrine in isotonic solution of crystalloid (e.g. physiologic saline, lactated Ringer's solution, Hartman's solution, etc) directly into subcutaneous fat or muscle or along the exterior length of a vein to produce swelling and firmness, or tumescence, of the targeted tissues, and thus produce very slow systemic absorption as a result of intense subcutaneous vasoconstriction, as well as direct hydrostatic compression of capillaries and veins.

Tumescent drug delivery, tumescent delivery: Tumescent drug delivery and tumescent delivery are synonyms referring to the tumescent technique for delivering a drug or combination of drugs into the subcutaneous space or other tissues. In other words, tumescent delivery is a process of infiltrating large volumes of dilute solutions of therapeutic substances, which may be dissolved in a crystalloid solution, into tissue (e.g. subcutaneous tissue) to the point of producing tumescence of the targeted tissue. Drugs other than lidocaine (e.g. photodynamic drugs, phototoxic drugs, chemotherapeutic drugs and antimicrobial drugs) can be administered by means of tumescent delivery, that is, by subcutaneous infiltration of dilute drug, with or without a vasoconstrictor such as epinephrine.

Tumescent drug: A tumescent drug is a drug dissolved in a dilute tumescent solution for the purpose of being delivered to the targeted tissue using the tumescent technique. Examples of diluents include physiologic saline (NaCl) or lactated Ringer's solution (LR).

Tumescent local anesthesia (TLA): A local anesthesia produced by direct infiltration into subcutaneous tissue of a volume of dilute lidocaine or other anesthetic drug (which may be less than or equal to 1 gram/liter) and a potent vasoconstrictor, such as epinephrine (which may be less than or equal to 1 milligram/liter), with a buffering agent, such as sodium bicarbonate (which may be between 10 to 25 milliequivalents/liter), in a crystalloid solution such as physiologic saline (NaCl) or lactated Ringer's solution (LR). In some embodiments higher concentrations of lidocaine or epinephrine can be used, it is generally safer to use the least (lowest) effective concentration.

Tumescent liposuction: Liposuction performed under local anesthesia using tumescent local anesthesia.

Tumescent fluid, tumescent solution: Dilute solutions of therapeutic substances dissolved in a solution, such as a crystalloid solution, intended for tumescent delivery into subcutaneous tissue.

Infiltration: An injection that causes a fluid to permeate or percolate through pores or interstices. In one embodiment, infiltration refers to injection of a fluid directly into a tissue.

Infusion: An injection that delivers a fluid into a place or into a body lumen, e.g., of a blood vessel. In one embodiment, infusion refers to an intravascular injection.

Injection: The action of forcing a fluid into a tissue, cavity or lumen, as by means of a syringe or by some impulsive force such as a peristaltic pump.

Switch and Device/Method Related Terms

Trigger mode (finite duration actuator): The switch is turned on by pressing once and remains on for a predetermined finite duration of time and then is turned off automatically. In this mode the rate of pump flow can be continuous or variable such as a repeating wave-form.

Radio button mode (on-off actuator): The switch is turned on by pressing once and remains on until pressed a second time.

Persistent pressure mode (on-off actuator): The switch is turned on by applying pressure to the button, and remains on until the pressure is removed.

Gas pedal mode (variable actuator): The switch provides a gradual increase in speed in response to a gradual increase of pressure applied to the switch device. Instead of an all-or-none on-off switch, the gas pedal switch provides for a continuously increasing response ranging from off to very slow to moderately fast to very fast to full speed, depending on the degree of pressure applied to the switch.

Bellows (singular): A structural member configured to furnish a strong blast of air.

Pneumatic: Air-operated

Bellows switch or pneumatic switch: An air-operated, on-off switch control that permits remote switching of an electric or other switchable device. In preferred embodiments, the bellows switch is safe and operable in a wet, sterile, and/or hazardous environment.

Bellows actuator, bellows trigger, pneumatic actuator, pneumatic trigger: A primary (e.g. hand held) switch or actuator which activates a second more distant switch which actuates a machine or device.

Double sequence switch: A first switch which activates a second switch which in turn actuates a machine or device.

Circuit-closer: Any device for closing an electric or optical circuit.

Elastomeric: A substance having rubber-like elastic properties.

One-way check valve: A valve to prevent backward flow of air or fluid in a tube.

Ball-valve: A valve that is opened or closed by the rising or falling of a ball that fits within a cup-shaped seat.

Embodiments of the invention relate to a remote actuator for a pneumatic switch for use in conjunction with a device that has a tube and a functional member. The remote actuator may include a bellows comprising a pneumatically sealed elastomeric pouch having at a first end thereof a pneumatic port. The pneumatically sealed pouch may also have a second end. The remote actuator may further include a means for selectively and reversibly attaching the bellows to the tube or functional member of the device. In some embodiments the attachment means is provided on the surface of the elastomeric pouch. In several embodiments the elastomeric pouch is configured to form a channel through which the functional member or a segment of the functional member of the device may pass.

In some embodiments, an actuating tube is pneumatically coupled to the pneumatic port of the bellows at one end and the pneumatic switch on the remote device at the other end. The actuating tube is adapted to conduct an air pressure pulse created by compression of the bellows from the pneumatic port thereof to the pneumatic switch on the device. The ends of the actuating tube are preferably reversibly fixable to the pneumatic port of the bellows and the pneumatic switch on the device.

The bellows may further include a fluid inlet port, a fluid conduit, and a fluid outlet port. In some embodiments, the fluid conduit traverses the bellows between the fluid inlet port and the fluid outlet port to allow fluid communication there between. The fluid inlet port may be adapted to receive a fluid supply tube fixed to a fluid reservoir. The fluid outlet port may be adapted to be selectively coupled to the treatment member of the medical device, e.g., an infiltration cannula.

In another embodiment, the pneumatic port and the fluid inlet port may be integrally formed. In this embodiment, the actuating tube preferably includes at least two internal lumens or conduits mutually isolated therein. A first conduit of the two internal conduits is for conducting the air pressure pulse created by the bellows from the pneumatic port of the bellows to the pneumatic switch. A second conduit of the two internal conduits is for conducting the fluid from the fluid inlet port through the bellows and to the fluid outlet port. In another embodiment, the first of the two internal conduits includes at least one port or aperture within the bellows for conducting the air pressure pulse created by the bellows therethrough.

In another embodiment, the elastomeric bellows further includes a length of substantially cylindrical tubing. The tubing may include a pair of hermetically sealed end caps with a first of the end caps including the pneumatic port therein.

In another embodiment, a remote actuator is designed for at least two pneumatic switches for use in conjunction with at least two medical devices. In this embodiment, the remote actuator includes at least two bellows. Each bellows may include a pneumatically sealed elastomeric pouch having at a first end a pneumatic port, and a means for selectively attaching each bellows to each medical device. The remote actuator may also include at least one actuating tube, each actuating tube having a bellows end and a device end. Each bellows end may be coupled to the pneumatic port of one of the bellows. Each actuating tube is preferably adapted to conduct an air pressure pulse created by the bellows from the pneumatic port thereof to the device end thereof. Each device end is preferably designed to facilitate pneumatic coupling to one of the pneumatic switches. With each bellows attached to each medical device, each bellows can be squeezed to actuate one of the pneumatic switches. The number of bellows and actuating tubes would correspond to the number of medical devices desired to be remotely activated.

In a further embodiment, each bellows may be mutually fixed acting as a handle for manual manipulation of the treatment member of the medical device (e.g., infiltration or suction cannula). In another embodiment, the remote actuator includes a rigid manifold handle segment adapted for receiving at least one bellows thereon. In some embodiments, the outer surface of the handle segment comprises a series of ridges and valleys. The handle segment may traverse an aperture channel formed through each bellows. In several embodiments the handle segment and the bellows are pneumatically separate. In some embodiments, the bellows and the handle segment are pneumatically coupled. In some embodiments, the handle segment may include a plurality of conduits therethrough open at apertures thereof. Each aperture is preferably for conducting the air pressure pulse created by the bellows through the handle and to the respective actuating tube and for pneumatic communication therewith. In another embodiment, the remote actuator further includes a detachable handle segment attached to the fluid outlet port.

In another embodiment, a disposable bellows switch can also be adapted as an on-off switch for a medical laser. The laser light is transmitted along an optical fiber which is located within and passes along a disposable sterile plastic tube, this tube being incorporated with an elastomeric bellows, which may also function as a handle for the optical fiber.

Some embodiments relate to a disposable, single-use, pneumatic, bellows-action, hand-held remote control on-off switch that is safe, inexpensive, light-weight, small, reliable and having few moving parts, that can be easily and accessibly attached to a reusable surgical device. Alternatively, the switch can be easily and inexpensively incorporated into a large variety of disposable surgical devices. In some embodiments, non-conducting materials are used in making the switch, to avoid or reduce the risk for electric shock, while allowing a remote device to be activated and deactivated as desired.

A bellows is configured to furnish a relatively strong or sufficiently strong pulse of air to accomplish a task. A bellows can send a pulse of air pressure along a hollow tube that is sufficient to displace an air-pressure sensitive diaphragm of a pneumatic switch and thereby close or open an electric, optical, or mechanical circuit. A bellows switch as used herein is an air-operated, remote control on-off switch that permits remote switching of any switchable device. The need for such a device is most apparent for operations in an environment that is wet, sterile, and/or hazardous (e.g., explosion hazard). The terms bellows switch, air switch, pneumatic switch, pneumatic actuator maybe used herein as synonyms, although the bellows is typically used herein to describe the component of the remote actuator configured to be held by the surgeon/operator, whereas the pneumatic switch is typically used herein to describe the air pressure operated switch on the electrical medical device.

A remote actuator can be constructed out of plastic, silicone, nylon, metal, plant fiber, or any appropriate substance, wherein the bellows component is preferably made of an elastomeric material such as latex, styrene-butadiene rubber, acrylonitrile, butadiene styrene, acrylic polymers, polyisoprene, chloroprene rubber, polychloroprene, neoprene, polyvinyl acetate, butyl rubber, ethylene propylene rubber, silicone rubber, polyacrylic rubber, fluorosilicone rubber, ethylene vinyl acetate, thermoplastic elastomers or any appropriate elastomeric substance. For medical applications, it is desirable that the bellows of the remote actuator be water proof and sterilizable, e.g., by electron-beam or gamma radiation, and not be a conductor of an electric current. A bellows may be a closed (air-tight) system or it may be an open system equipped with a one-way check-valve that lets air into the system when the bellows expands. A bellows can be a closed system or an open system. When a bellows is constructed of a plastic-like material with elastomeric qualities, the resting configuration of the bellows can be substantially expanded. Actuation of the bellows occurs when the bellows is manually compressed or otherwise squeezed.

The bellows may be held in a hand and actuated by squeezing, used as a floor pedal and actuated by stepping on the bellows switch with a foot, or held in a mouth and actuated by biting on the bellows switch. For example, a mouth actuated bellows switch may be used as a "nurse-call-button" by patient in a hospital bed who has distal extremity injury, weakness or neurological impairment such as a quadriplegic patient or a stroke patient. A disposable sterile bellows switch can be held in a surgeon's mouth to be actuated by biting and thereby allow the surgeon to use both hands while performing a procedure that requires careful, concomitant and dexterous use of both hands. The bellows switch can be used to actuate any switchable device including mechanical devices, light or laser devices, compressed air, gas, or vacuum devices, or devices that involve fluid flow, heat, cold or chemical processes, as well as other switchable devices.

A remotely actuated bellows switch (remote actuator) together with an associated diaphragm air switch (pneumatic switch) comprise a "double sequence switch" wherein the bellows activates the diaphragm of the pneumatic switch, which may in turn actuate a machine or device. A bellows switch can be programmed to have multimodal functionality. Thus, depending on the task or application requirements, a person operating a bellows switch may be able to select one of several possible switching modes.

One possible mode is a radio-button on-off switch mode whereby the switch is turned on by pressing once and remains on until pressed a second time which turns off the switch. A second possible mode is a momentary on-off switch mode whereby the switch is turned on by applying pressure to the button, and remains on until the pressure is removed which results in the switch being turned off. A third possible switching mode is a "gas-pedal" or proportional-pressure bellows control mode. In contrast to a simple on-off switch, some devices operate at variable-speed and require a variable-speed remote control. A bellows switch can be designed to permit controlling a variable speed device by simply varying the pressure applied to the bellows switch. The rate or speed of the machine can be linearly proportional response to, or non-linearly proportional response to the pressure applied to the bellows switch. In a linearly proportional switch mode, an increasing degree of squeezing or hand pressure on the hand held bellows switch produces a proportionally increasing degree of air pressure on the diaphragm machine-switch which in turn produces a proportional increase in the power, speed or intensity of the machine action. Another mode is a trigger on-off switch in which a single activation results in a time-limited machine response.

Aspects of the disclosed remote actuator or bellows switch include that it is constructed with very few parts, it is inexpensive, it may be disposable, it may be sterile or sterilizable, and its construction can be easily modified to accommodate the technical requirements of many different tasks or procedures. In some embodiments the bellows switch may be reversibly combined with a variety of switchable medical devices. Some switchable medical devices are intended to be used for multiple different procedures, and some switchable devices incorporate a handle that is intended to be reusable and re-sterilized. Reusable surgical devices virtually always have reusable on-off switches, for example foot-pedal switches, or hand-held switches that must be soaked, scrubbed, washed, rinsed, and re-sterilized by steam autoclave. A novel aspect of the remote actuators disclosed herein is their ability to be easily, rapidly and inexpensively combined or incorporated with the handle of another surgical devise resulting in a simple combination product that is safer, and easier to use.

In other aspects, the disclosed switches may be disposable, but not sterile, for use in remote actuation of non-sterile medical and industrial devices.

If a surgical device has a hand-held member such as a handle attached to the device by a cord, then a hand-held surgical device with a hand-held on-off switch is often easier to use than surgical device with a foot-pedal switch. In accordance with aspects of the present invention, a non-sterile foot-pedal switch may be replaced by a sterile disposable bellows switch that is attachable to the handle, medical tube, or other aspect of the surgical device. Any of the various embodiments described herein can be easily modified to include an attachment part that permits a disposable remote actuator to be attached to the handle of the surgical device or to the handle's connecting tubing. Many types of attachment members can be used. The choice of attachment member to be used is dependent upon the shape and design of the surgical device.

A disposable bellows on-off switch can be incorporated into the handle of an infiltration cannula used in the process of infiltration of tumescent local anesthesia (TLA), and thus the need for a foot-pedal switch can be eliminated. The use of a foot pedal on-off switch is cumbersome and potentially dangerous because of the risk of tripping or becoming entangled with cords connecting the foot-pedal to the device which it controls. As an anesthetist moves about a surgical operating table in order to be optimally positioned to accurately direct and manipulate the infiltration cannula, the foot pedal must be pushed, kicked or dragged along the floor adjacent to the table in order that the pedal is easily accessible to the anesthetist. When the anesthetist is standing during the process of tumescent infiltration, it is inconvenient and potentially dangerous to repeatedly reposition the foot pedal. The situation is much worse when the anesthetist performing tumescent infiltration is seated on a surgical stool having wheel-castors. While moving the stool about the table, the seated clinician must stretch a leg in order to reach the pedal. This maneuver is awkward and can cause the clinician to slip, inadvertently change position, or cause the clinician's feet or the stool's legs or wheels to become entangled with the foot pedal cord. There is also the ever present risk that other operating-room personnel can trip on the foot pedal cords.

Furthermore, if there is more than one surgical device that is operated by a foot-pedal on-off switch, then there are the risks of a) stepping on the wrong pedal, b) pedal cords becoming entangled, and c) having to take one's eyes and attention diverted away from the patient in order to locate the correct pedal. Another important advantage of a hand-held on-off switch is that hand-eye coordination is more accurate than foot-eye coordination.

Embodiments of the sterile disposable hand-held remote actuators have the potential advantages of preventing two types of hospital acquired infections in surgical patients. The most common types of hospital acquired infections are non-surgical nosocomial infections including potentially fatal pneumonias and gastrointestinal infections, especial Clostridium difficile (Pseudomembranous colitis). Nosocomial infections are infections which are a result of treatment in a hospital or a healthcare facility, but not secondary to the patient's original condition. A non-surgical nosocomial infection is typically passed from patient to patient within a hospital by environmental contamination or by direct contact with contaminated health care providers.

The second type of nosocomial infection is widely known as a surgical site infection (SSI). Surgical site infections most commonly involve the skin and subcutaneous tissues at the site of a surgical incision, but infections of deeper tissues, such as peritonitis, can also occur. The present standard of care for SSI prophylaxis is an IV infusion of an antibiotic 30 to 60 minutes prior to surgical incision; however IV antibiotics are relatively inefficient (because relatively low and short duration antibiotic tissue levels) and are associated with increased risk of *C. difficile* infections (because of relatively high antibiotic blood level which disturb the ecology of gut bacteria and promote *C. difficile* overgrowth). A much more efficient and safer means of SSI prevention is tumescent antibiotic delivery (TAD), see e.g., U.S. Provisional Application No. 61/256,286 and International Application Number PCT/US10/58440; incorporated herein in its entirety by reference.

Tumescent antibiotic delivery (TAD) is used herein to refer to the subcutaneous delivery of an antibiotic in a solution of tumescent local anesthesia (TLA). Because TLA contains a potent vasoconstrictor, like epinephrine, the antibiotic within the TLA solution lingers at the site of infiltration for many hours at concentrations which exceed the tissue concentrations following IV delivery by an order of magnitude. Further, the very high tissue antibiotic concentration associated with TAD persists for many hours beyond the relatively brief duration of "sufficient" tissue concentrations which follow IV delivery. Furthermore, TAD is associated with relatively low blood concentrations of the antibiotic and therefore it is associated with decreased risk of potentially fatal *C. difficile* infection. Thus, TAD reduces the risk of SSI by producing very high and persistent antibiotic concentrations exactly at the site of a surgical infection, and concomitantly TAD is safer than IV delivery by reducing the risk promoting bacterial antibiotic resistance and reducing the risk of *C. difficile* infections.

By reducing the occurrence of peristaltic pump contamination, aspects of the present invention will help reduce the risk of non-surgical nosocomial infections among surgical patients who receive TAD for prevention of SSI. TAD may be accomplished by a nurse in a patient's hospital room rather than in the surgical operating room because it is safer, and more economical. In a hospital room environment special care must be taken to avoid transmissions of nosocomial infection from contaminated hospital floors and furniture. TAD is achieved with a peristaltic tumescent infiltration pump whereby sterile peristaltic tubing transports the TAD solution from a distal reservoir (IV bag-like container) through the peristaltic pump and out through the proximal tubing via an infiltration cannula which has been inserted within the targeted subcutaneous tissue.

The conventional technique for actuating the peristaltic pump requires a foot switch on the floor. Each time the pump is moved from one patient's room to another patient's room the nurse must use his/her hands to pick-up the foot switch. The nurse will also use her hands to push the cart-mounted peristaltic pump from one room to the next. In this fashion there is a risk that the cart and the peristaltic pump will become contaminated and become a source for transmitting nosocomial infections. A safer and more time-efficient on-off switching device for the peristaltic pump would be a hand-held sterile bellows switch incorporated into the peristaltic pump tubing wherein the proximal male luer lock connector is conjoined with the bellows switch to function as a cannula handle during the tumescent infiltration process.

Liposuction is a surgical procedure that involves the removal of subdermal fat by means of a specialized stainless steel liposuction cannula and a suction device. The length of a typical liposuction cannula ranges between 15 to 30 centimeters (cm). The distal tip of the cannula has a blunt point. The distal 2 to 6 cm portion of the cannula has one or more small round or oblong holes or fenestrations. The proximal end of the cannula can be detachably connected to the distal end of a cannula-handle by means of a Luer-type connection. The proximal end of the cannula handle has a hose-bib attachment by which it is connected to a long flexible plastic hose, which in turn is attached to a powerful vacuum aspirator. The aspirator is generally actuated by means of a reusable foot pedal on-off switch. A bellows-action remote actuator can be incorporated into a sterile, disposable handle of a liposuction cannula, thereby eliminating the need for a foot-pedal on-off switch, and the expensive time-consuming logistic process of cleaning, wrapping, sterilizing and transporting reusable liposuction handles.

Liposuction surgery requires the insertion of the cannula through a skin incision into the subdermal fat, then actuating the vacuum aspirator, and advancing and retracting the cannula throughout the targeted compartment of fat in a skillful manner. Fat is removed by a process in which small lobules of fat are sucked through a cannular fenestration and then torn from their tissue attachment as the surgeon forcefully pushes and pulls the cannula in a continuing in-and-out motion. Manufacturing a disposable liposuction handle with an incorporated bellows on-off switch eliminates the need for a foot-pedal on-off switch, eliminates the need to sterilize the reusable cannula handles, and allows more convenient on-off switching. Similarly, other types of disposable tool handles can be manufactured with an integrated disposable on off switch.

By incorporating disposable bellows on-off switches into the distal end of a tumescent infiltration tube as well as incorporating disposable bellows on-off switches into a liposuction cannula handle, one can eliminate the great inconvenience and risks of having multiple tubes and cords continuously underfoot during surgery. Thus, a liposuction cannula handle and its associated fat-transporting tube can be combined with an on-off bellows switch and its associated air-transporting tube. These two transporting tubes being conjoined side-by-side in a parallel fashion leading from the disposable liposuction handle toward the liposuction aspiration machine. In another example, a tumescent local anesthesia infiltration cannula handle can have a disposable on-off switch which effectively eliminates the necessity of foot pedal switches and the tangle of tubing lying on the floor.

Some embodiments relate to a disposable bellows on-off switch that can be reversibly combined with a variety of reusable handles for liposuction cannulas and infiltration cannulas. A disposable on-off switch that is a separate element from a reusable handle, allows the reusable handle to incorporate fewer working components, thus decreasing manufacturing costs and increasing the ease of cleaning and sterilization.

Some embodiments relate to a disposable bellows switch that can be incorporated into the handle of almost any surgical device including laser, electrocautery devices, power drills, saws, and vacuum aspirator devices, fluid transport or irrigation devices, light or illumination devices. In some embodiments, two or more color-coded disposable bellows switches can be combined into one hand-held device that has several modes of action. For example, an endoscopic surgical device that incorporates into one handle the ability to flush the abdominal cavity with physiologic saline and then aspirate the water out of the abdomen.

In addition to surgical devices, there are a large number of other devices which would benefit from having a sterile disposable single-use bellows-action (pneumatic) hand-held remote control on-off switch that is safe, inexpensive, lightweight, small, reliable and with few moving parts. Hospital devices that would benefit from such switches include: patient controlled analgesic/narcotic delivery device, patient controlled nurse-call button, patient controlled television remote control (on-off switch, sound volume control, channel selector), and patient controlled bed-positioning mechanism. In many hospitals such devices are not disposable, are not sterilized between successive use by different patients, and therefore these reusable devices are possible sources for communicating hospital acquired (nosocomial) infectious diseases.

Unless the context clearly requires otherwise, throughout the description and the claims, the words "comprise," "comprising," and the like are to be construed in an open, inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

With respect to the drawings, FIGS. 1A-1F illustrate a remote actuator 10 for a pneumatic switch 20 on the electrical portion of a medical device (e.g., a peristaltic pump, not shown) for use in conjunction with a medical treatment member 30 having a medical tube 35. The remote actuator 10 includes a bellows 40 comprising a pneumatically sealed pouch 50 with a pneumatic port 60 at a first end 52, which port is pneumatically coupled to an actuating tube 80. The actuating tube 80 pneumatically couples the bellows 40 to the pneumatic switch 20 for actuating the medical device (not shown). The pneumatically sealed pouch 50 also has a second end 58, which is typically sealed and may in some embodiments comprise a handle portion (not shown). The remote actuator 10 further includes a means 72 for reversibly attaching the remote actuator 10 either directly to the medical treatment member 30 (or the medical tube 35 of the treatment member—as illustrated in FIG. 1A). In some embodiments, a connector element 110 may be used to couple the distal end region of the medical tube 35 to the medical treatment member, e.g., a tumescent anesthesia infiltration cannula or a liposuction cannula. In other embodiments (not shown), the medical treatment member 30 is integral and continuous with the medical tube 35. The means for reversibly attaching the remote actuator 10 to the medical treatment member 30 or the medical tube 35 can include a threaded screw type connection, a snap type connection, and other suitable type connections depending on the medical device. In one embodiment, the means for reversibly attaching the remote actuator 10 to the medical tube 35 is a C-shaped resilient clamp 72 (FIG. 1F) adapted to clamp around the medical tube 35 which is connected to the medical treatment member 30 at the distal end and the medical device at the proximal end (e.g., a peristaltic pump).

In a variation, the actuating tube 80 may be co-extruded with a plastic (or glass) optic fiber that carries light to the hand-held bellows 40, thereby providing illumination to a preferably clear plastic bellows. Such an optic fiber could be used to illuminate e.g., a nurse-call device, help locate a light switch in the dark or provide indication of the on-off status of the switch.

In another embodiment, illustrated in FIGS. 7A-7G, the bellows 40 further includes a length of substantially cylindrical tubing 160. The substantially cylindrical tubing 160 includes a pair of sealed end caps 170 and 171, with a first 171 of the end caps including the pneumatic port 60 therein, illustrated in FIG. 7A. The actuating tube 80 may further include a distal coupling 172 to facilitate reversible coupling of the actuating tube to the pneumatic port 60 of the end cap 171, as illustrated in FIG. 7E.

Figure 2A:
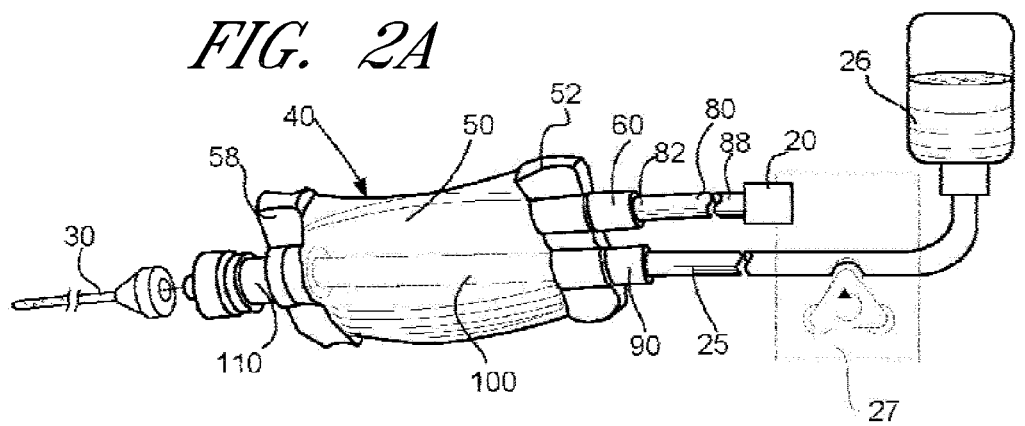
FIG. 2A shows a partially transparent perspective view of a remote actuator, illustrating an actuating tube, a fluid outlet port, a fluid inlet port and peristaltic infiltration tubing.

FIG. 2A illustrates an actuating tube 80 having a proximal end 82 and a distal end 88. The proximal end 82 is fixed to the pneumatic port 60 of the bellows 40. The actuating tube 80 is adapted to conduct an air pressure pulse created by the bellows 40 from the pneumatic port 60 thereof to the distal end 88 thereof. The distal end 88 is configured to couple to the pneumatic switch 20 that controls the electrical device 27 (here a peristaltic pump), illustrated in FIG. 2A. With the bellows 40 attached to the medical treatment member 30, the bellows 40 can be squeezed to actuate the pneumatic switch 20.

Figure 2B:
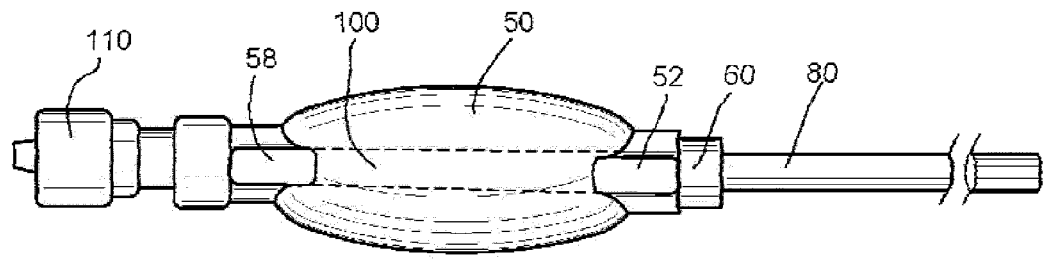
FIG. 2B shows a side elevational view of a remote actuator, illustrating an actuating tube and a fluid outlet port.
Figure 2C:
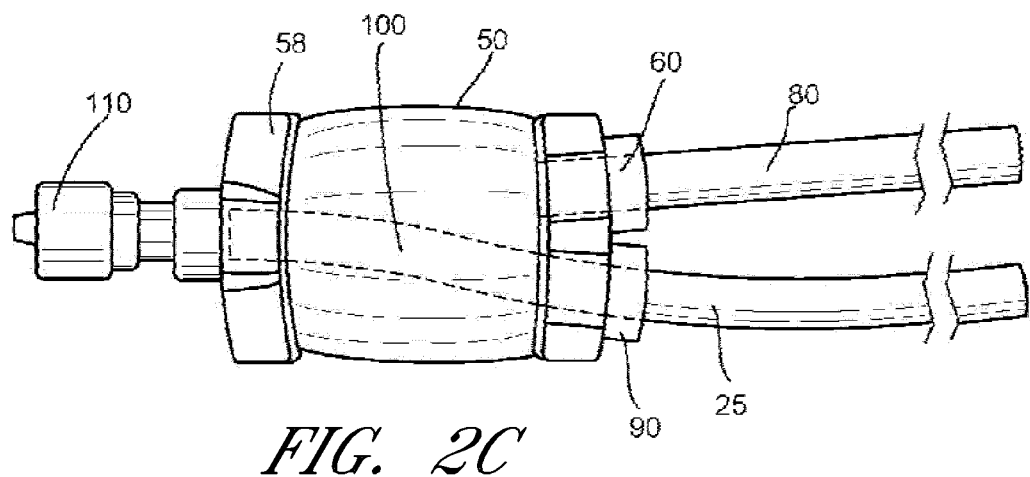
FIG. 2C shows a partially transparent top plan view of a remote actuator, illustrating an actuating tube, a fluid outlet port and a fluid inlet port.
Figure 3C:
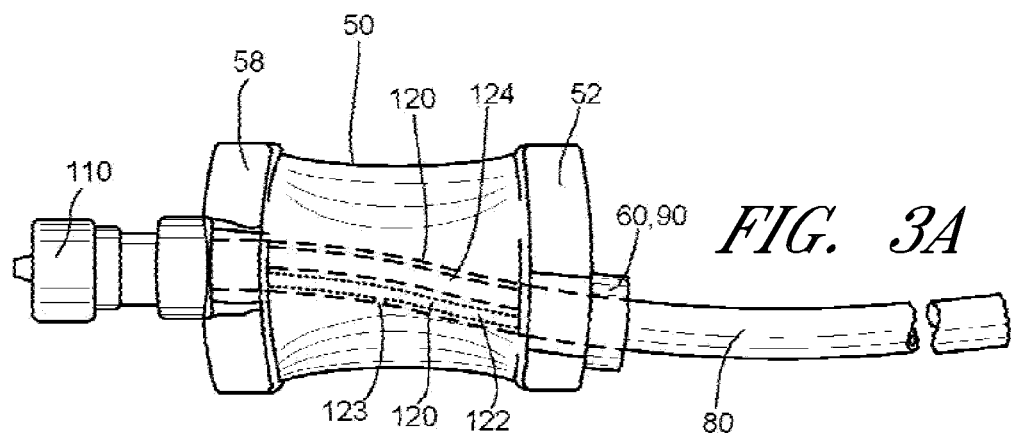
FIG. 3C shows a cross section diagram showing an occluder in an internal conduit, taken generally along lines 3C-3C of FIG. 3B.
Figure 3D:
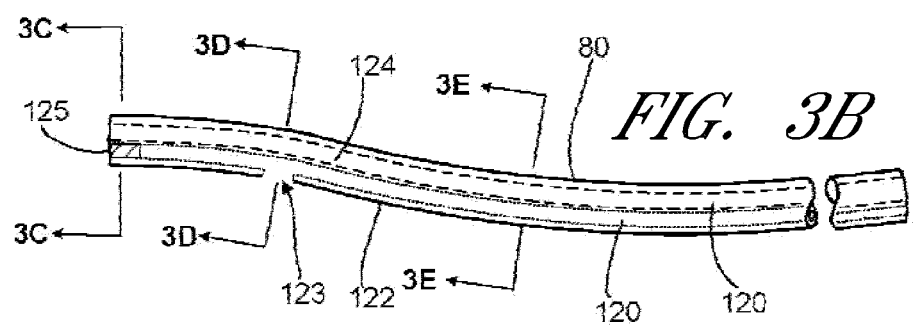
FIG. 3D shows a cross section diagram showing an aperture in an internal conduit, taken generally along lines 3D-3D of FIG. 3B.
Figure 3E:
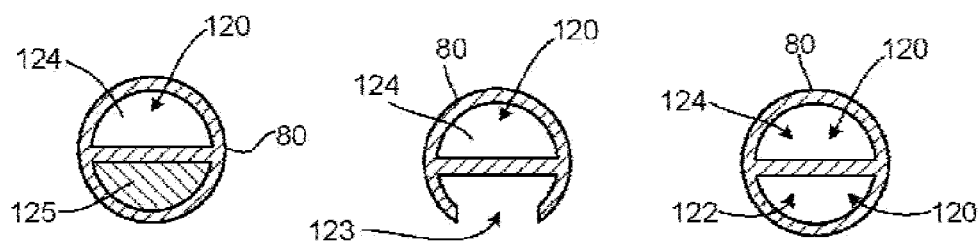
FIG. 3E shows a cross section diagram showing internal conduits, taken generally along lines 3E-3E of FIG. 3B.
Figure 5A:
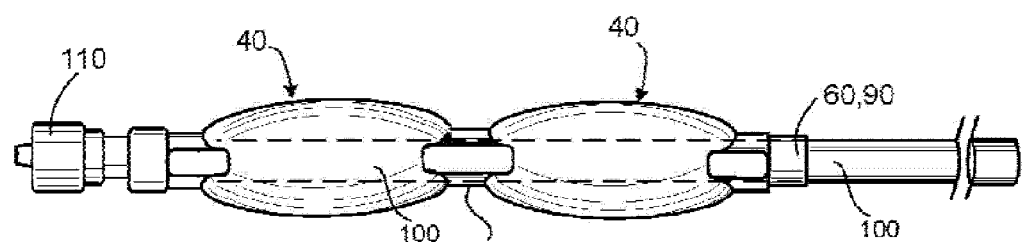
FIG. 5A shows a partially transparent side elevational view of a remote actuator, illustrating an actuating tube, two bellows, and a fluid outlet port.
Figure 5B:
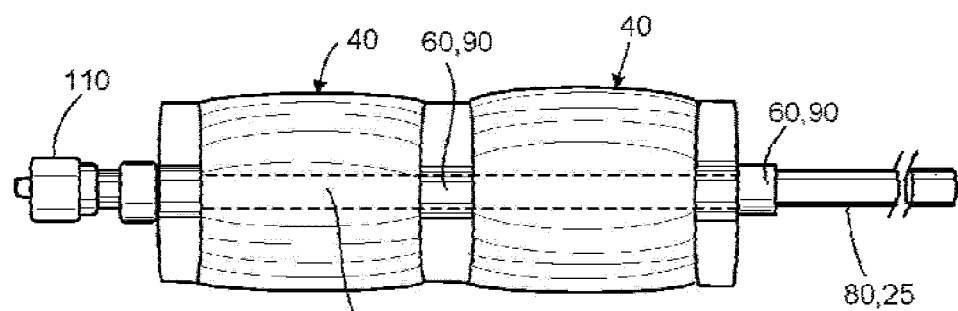
FIG. 5B shows a partially transparent top plan view of a remote actuator, illustrating an actuating tube, two bellows, and a fluid outlet port.

In FIGS. 2A-2C, the bellows 40 further includes an inlet port 90, an internal conduit 100, and an outlet port 110. The internal conduit 100 traverses the inside of the bellows 40 between the inlet 90 and outlet ports to allow fluid communication there between. Illustrated in FIG. 2A, the inlet port 90 is adapted to reversibly receive a medical tube 25. In the illustrated embodiment, the medical tube 25 connects the inlet port with a fluid reservoir 26. The outlet port 110 is adapted to be reversibly fixed to the treatment member 30 (a tumescent anesthesia infiltration cannula). When the pneumatic switch is actuated a pump 27 moves the fluid (e.g., tumescent fluid) from the reservoir 26 toward the treatment member 30 (e.g., the infiltration cannula). The embodiment illustrated in FIGS. 2A-2C may be a sterile remote actuator configured to be hand-held by a clinician during the delicate process of delivering a large volume of tumescent local anesthesia to the subcutaneous tissues of a fully-awake and alert patient prior to surgery; this infiltration process requires skill and finesse with repeated on-off switching of the peristaltic pump.

Of course, the remote actuator illustrated in FIGS. 2A-2C, may also be used e.g., for actuating any other device for delivering (infusing, infiltrating, etc.) or withdrawing (suctioning) a fluid (e.g., a suction device—including a vacuum pump or a wall suction outlet).

In another embodiment, illustrated in FIGS. 3A-3E, the pneumatic port 60 and the fluid inlet port 90 are integrally formed. In this embodiment, the actuating tube 80 includes at least two internal conduits or lumens 120 (FIGS. 3A-3E) mutually isolated therein. A first conduit 122 (FIG. 3E) of the two internal conduits 120 is for conducting the air pressure pulse created by the bellows 40 from the pneumatic port 60 to the distal end 88 thereof. A second conduit 124 (FIG. 3E) of the two internal conduits 120 is for conducting the fluid from the fluid inlet port 90 through the bellows 40 and to the fluid outlet port 110. In another embodiment, the first 122 of the two internal conduits 120 includes at least one aperture 123 (FIGS. 3D and 4C) within the bellows 40 for conducting the air pressure pulse created by the bellows 40 therethrough. In another embodiment, the first conduit 122 further includes an occluder 125 (FIGS. 3B-3C and 4C-4D) in the conduit 122 for preventing the air pressure pulse from going into an undesired direction.

In another embodiment, illustrated in FIGS. 4A-4F, the remote actuator 10 is designed for two pneumatic switches for use in conjunction with two medical devices (e.g., a liposuction device and a tumescent anesthesia infiltration device). In this embodiment, the remote actuator 10 includes two bellows 40, one for each device; alternatively, the two bellows of a remote actuator could be used with only one device. Moreover, more than two devices or functionalities of a single device could be actuated remotely by incorporating additional bellows. Each bellows 40 includes a pneumatically sealed pouch 50 having at a first end 52 thereof a pneumatic port 60, and a means for selectively attaching each bellows to each device. The remote actuator 10 may include two actuating tubes 80, each actuating tube pneumatically coupling the pneumatic port 60 of one of the bellows 40 to the pneumatic switch on the device which it actuates. Each actuating tube 80 is adapted to conduct an air pressure pulse created by the bellows 40 from the pneumatic port 60 thereof to the pneumatic switch (not shown) at one end 88 thereof. Each of the proximal ends 88 is fixable to one of the pneumatic switches 20. With each bellows 40 attached to each medical device, each bellows 40 can be squeezed to actuate one of the pneumatic switches. The number of bellows 40 and actuating tubes 80 would correspond to the number of medical devices that are desired to be remotely activated using the remote actuator 10. In one embodiment, each actuating tube 80 is mutually fixed. In another embodiment, each of the two actuating tubes 80 is made from a co-extrusion process, in which a single integrated dual lumen tube extends at least part of the distance between the remote actuator bellows and the respective medical device. In another embodiment, the actuating tube 80 includes at least two conduits or lumen 122 (FIGS. 4C-4F) mutually isolated therein.

In one embodiment with the actuating tube 80 having at least two internal conduits 120 mutually isolated therein, the actuating tube 80 is connected at the proximal end 88 to a Y-type splitting tube (not shown) to connect the passageway of each internal conduit 120 to a desired pneumatic switch. In another embodiment with the actuating tube 80 having at least two internal conduits 120 mutually isolated therein, the actuating tube 80 is connected to a device (not shown) that splits each passageway of each internal conduit 120 as desired.

One example of the utility of the embodiment illustrated in FIG. 4A is as an inexpensive sterile disposable combination hospital-bed nurse-call button and hospital bedside light on-off switch which would reduce the risk of nosocomial infections.

In a further embodiment, illustrated in FIGS. 4A-4B and 5A-5B, each bellows 40 is mutually fixed. In one embodiment, each bellows 40 is mutually fixed acting as a handle for manual manipulation of the treatment member of a medical device. In another embodiment, the remote actuator includes exactly two bellows 40 mutually fixed, illustrated in FIGS. 5A-5B. In one embodiment, the two mutually fixed bellows 40 further include a single fluid inlet port 90, a fluid conduit 100, and a fluid outlet port 110. The fluid conduit 100 traverses the two bellows 40 between the fluid inlet port 90 and the fluid outlet port 110 to allow fluid communication there between. In the illustrated embodiments, the inlet ports 90 may be shared with the pneumatic ports 60.

Figure 6:
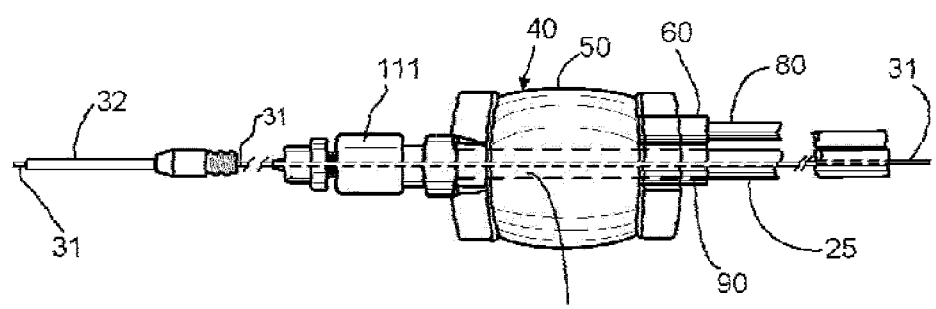
FIG. 6 shows a partially transparent top plan view of a remote actuator, illustrating an actuating tube, a bellows, a laser optic fiber outlet port, and a medical instrument.
Figure 8A:
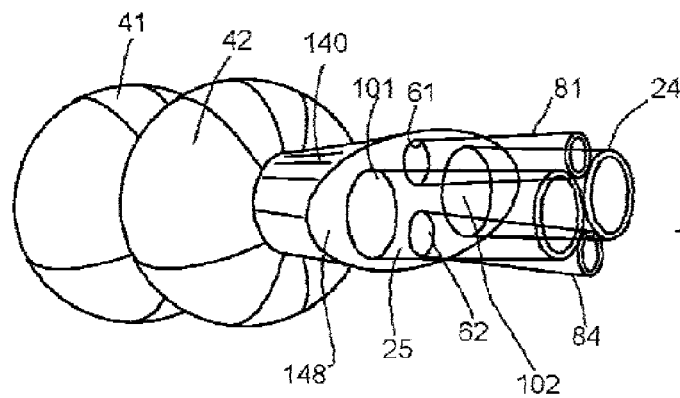
FIG. 8A shows a partially transparent perspective view of two bellows, two actuating tubes, two fluid inlet ports, and two fluid supply tubes, and a manifold handle.
Figure 8B:
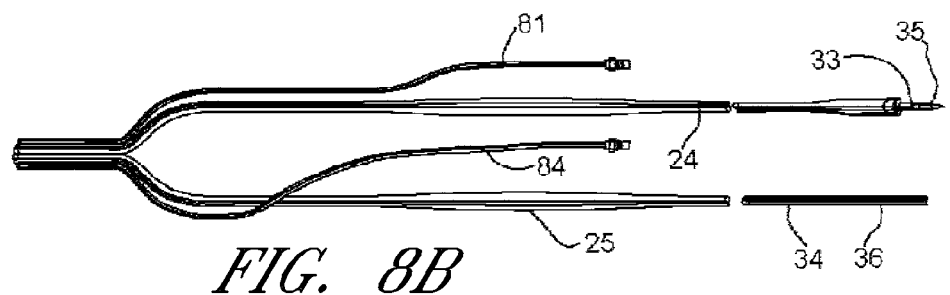
FIG. 8B shows perspective view of two actuating tubes, two fluid supply tubes, and two medical instruments.
Figures 8C, 8D:
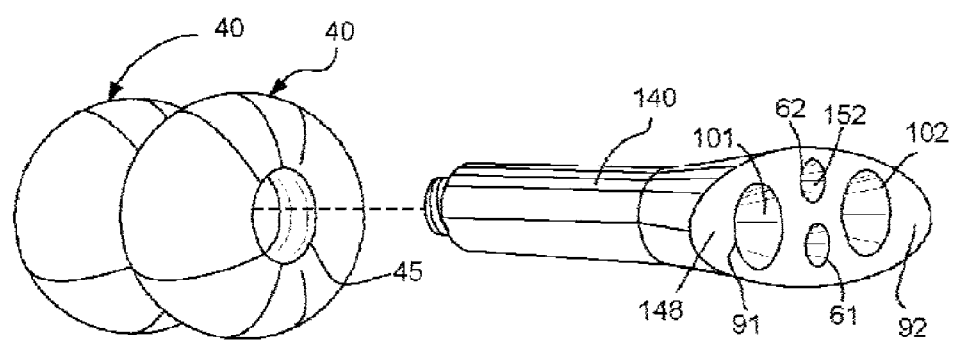
FIG. 8C shows a partial perspective view of FIG. 8A having two bellows mutually fixed.
FIG. 8D shows a perspective view of a manifold handle segment with two pneumatic ports and two fluid transport ports.
Figure 9A:
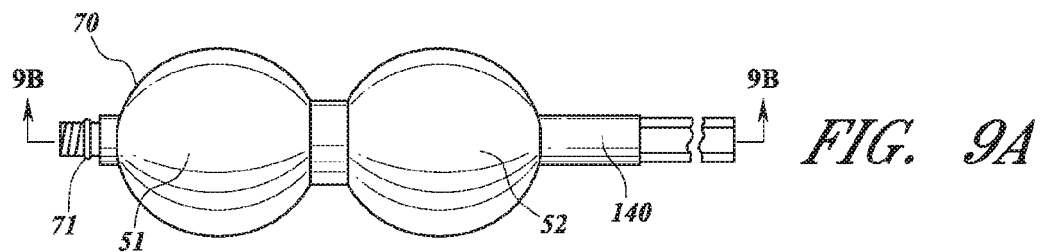
FIG. 9A shows a side elevational view of FIG. 8A consisting of two bellows mutually fixed to a manifold handle, actuating tubes, fluid transport tubes and an attachment means.
Figure 9B:
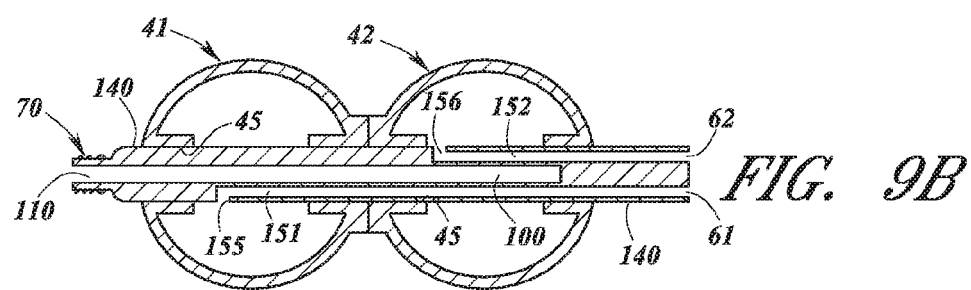
FIG. 9B shows a cross section side-view diagram showing a rigid manifold handle segment and two bellows, taken generally along lines 9B-9B of FIG. 9A.
Figure 9C:
FIG. 9C shows a side elevational view of a rigid manifold handle segment.
Figure 9D:
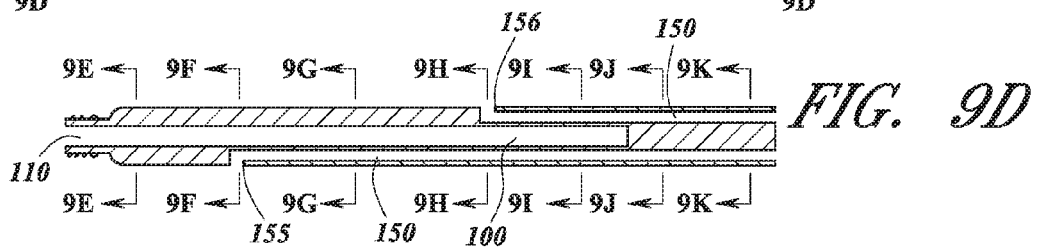
FIG. 9D shows a cross section diagram showing a rigid manifold handle segment, taken generally along lines 9D-9D of FIG. 9C.
Figures 9E, 9G, 9I, 9K:
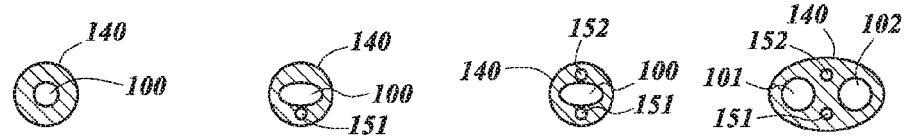
FIG. 9E shows a cross section diagram showing part of a rigid manifold handle segment, taken generally along lines 9E-9E of FIG. 9D.
FIG. 9G shows a cross section diagram showing part of a rigid manifold handle segment, taken generally along lines 9G-9G of FIG. 9D.
FIG. 9I shows a cross section diagram showing part of a rigid manifold handle segment, taken generally along lines 9I-9I of FIG. 9D.
FIG. 9K shows a cross section diagram showing part of a rigid manifold handle segment, taken generally along lines 9K-9K of FIG. 9D.
Figures 9F, 9H, 9J:
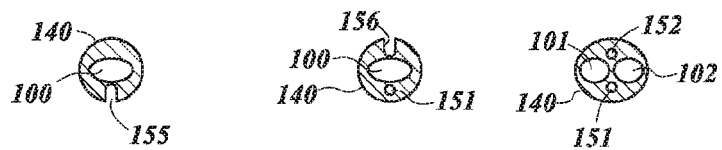
FIG. 9F shows a cross section diagram showing part of a rigid manifold handle segment, taken generally along lines 9F-9F of FIG. 9D.
FIG. 9H shows a cross section diagram showing part of a rigid manifold handle segment, taken generally along lines 9H-9H of FIG. 9D.
FIG. 9J shows a cross section diagram showing part of a rigid manifold handle segment, taken generally along lines 9J-9J of FIG. 9D.
Figure 10A:
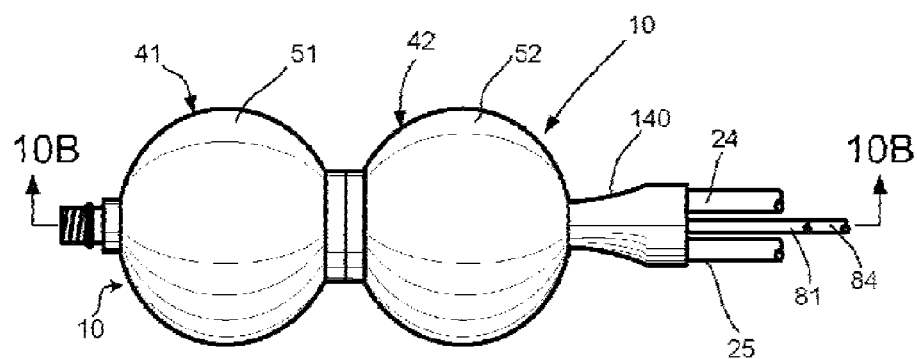
FIG. 10A shows a top elevational view of two bellows and a manifold handle segment.
Figure 10B:
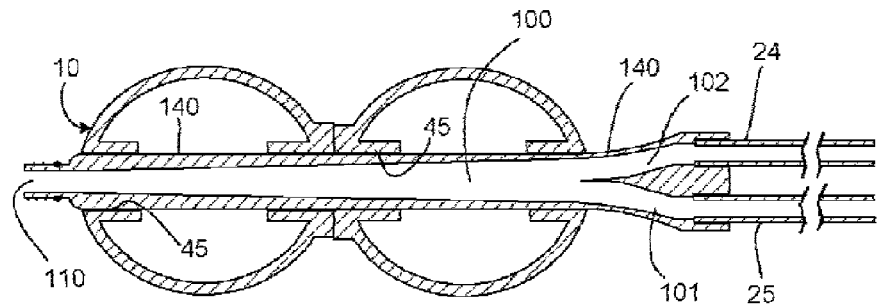
FIG. 10B shows a top cross section view diagram showing two bellows and a handle segment, taken generally along lines 10B-10B of FIG. 10A.

In the embodiment illustrated in FIG. 6, the medical tube segments 25 and 100 have been adapted to function as a conduit for a optical fiber surgical laser 31; the conduit is preferably sterile. The outlet port 111 comprises a collet or torquer which securely holds the optical fiber in place within the laser cannula 32 and prevents longitudinal movement of the optical fiber 31 within the laser cannula 32. Laser optical fibers are brittle, springy, ungainly and awkward to handle and thus difficult to manage within a sterile surgical field. Placing the optical fiber 31 within the transport or medical tube 25 improves the ease of manipulating the fiber within a sterile environment. The pneumatically sealed pouch 50 also functions as a sterile handle and a hand-held on-off switch which allows the surgeon to more precisely aim and more accurately actuate the laser.

In variations to the laser shown in FIG. 6, this embodiment can also be applied to electrocautery, radiofrequency, ultrasound and other medical devices which would benefit from the availability of sterile and/or disposable pneumatic remote switches.

In other embodiments, illustrated in FIGS. 8A-8C and 9A-9K and 10A-10B, the remote actuator further includes a rigid handle segment 140 adapted for receiving at least one bellows 40 (41 and 42 in illustrated embodiments) thereon. The handle segment 140 traverses an aperture 45 formed through each bellows. The handle segment 140 may includes a plurality of conduits, e.g., 151, 152 therethrough open at apertures, e.g., 155, 156 thereof within the respective bellows. Each aperture 155, 156 is for conducting the air pressure pulse created by the respective bellows 40 to an end 148 of the handle segment 140 adapted for reversible attachment to respective actuating tubes 81, 84 and for pneumatic communication therewith.

The embodiment illustrated in FIGS. 8A-D, 9A-K, 10A-B, 11 may be made, sold and used as an inexpensive, sterile and disposable surgical device, e.g., for endoscopic abdominal surgery which provides both a means for rapid pumping saline to flush blood from a surgical field and a means for rapidly suctioning the blood-tinged fluid out of the abdominal cavity. The embodiment illustrated in FIG. 11 has only two moving parts, the elastomeric pouches 51 and 52, thus it is much less expensive and easier to manufacture compared to analogous devices which are currently available on the market. One example is a hand-held remote actuator connected by copper wires to a disposable battery powered electric pump. This device is relatively expensive with many moving parts and requires special battery disposal procedures.

This embodiment (FIG. 11) is a remote actuator 10 comprising a pair of remote hand-held bellows actuators 41 and 42, the first actuator 41 actuates a peristaltic pump 27, via pneumatic actuating tube 81, which delivers sterile physiologic saline from a reservoir 26 through a surgical cannula 30 inserted inside the peritoneal cavity, while the second 42 actuates e.g., a roller clamp 37, via pneumatic actuating tube 84, opening a standard wall-suction 29 to aspirate the blood-tinged fluid from the peritoneal cavity into a collection canister 28.

The first bellows actuator 41 is another embodiment of the device illustrated by FIG. 2A. When the surgeon compresses the elastomeric pouch 51 of remote actuator 41 a puff of air pressure travels through air intake port 155 along air transport channel 151 out through the exit port 61 and along tube 81 thus actuating a pneumatic switch 20 of peristaltic pump 27. The peristaltic pump 27 transports sterile saline from a distal reservoir 26 through the saline transport tube 25 into the rigid manifold handle 140 at intake port 91 then along intake channel 101 and fluid conduit 100 finally exiting the rigid handle at fluid outlet port 110.

Figure 11:
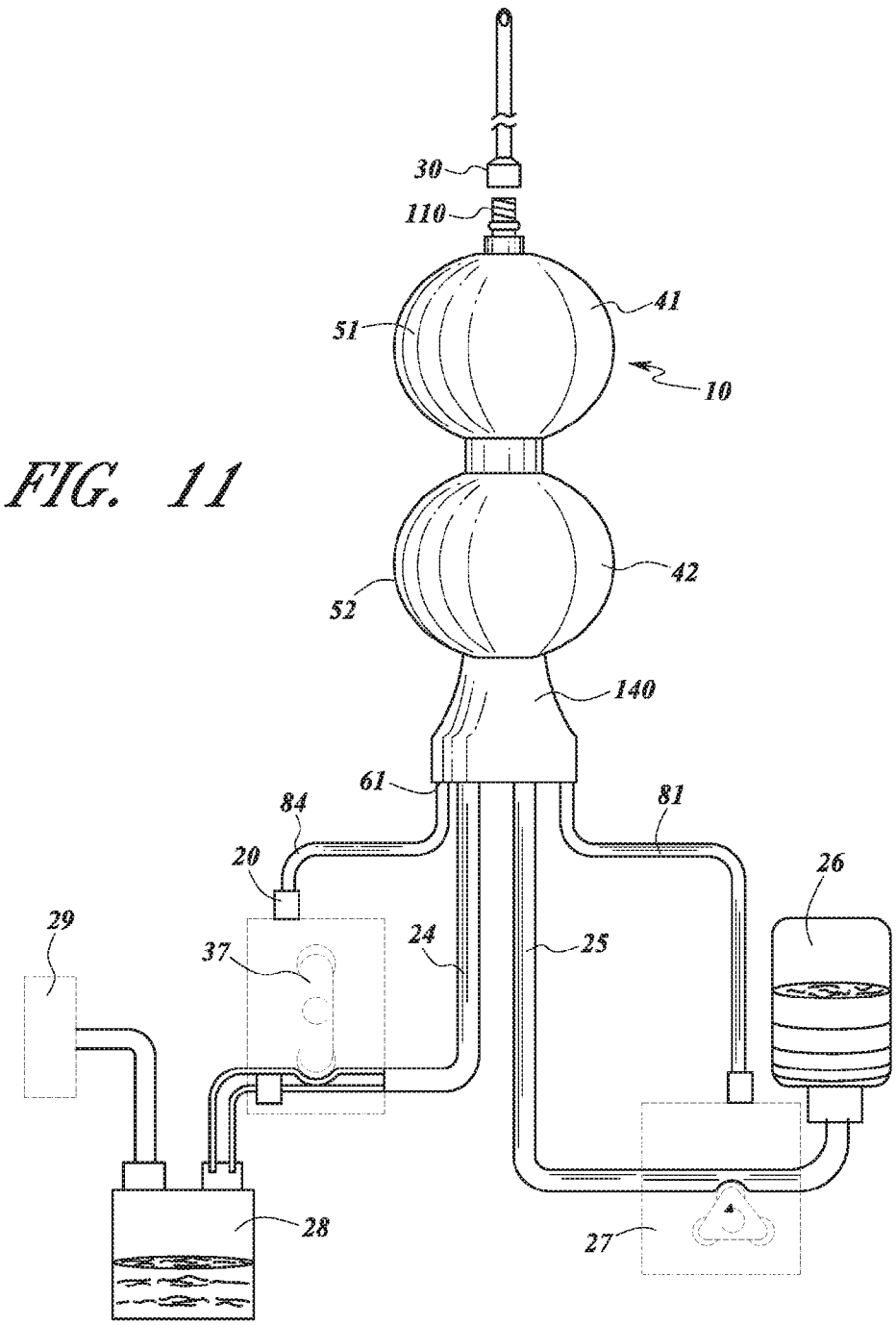
FIG. 11 shows an elevational view of the embodiment illustrated in FIGS. 8A-D, 9A-K, 10A-B showing its relationship to a peristaltic infiltration pump and a suction-aspirator.

When the surgeon squeezes the elastomeric pouch 52 of the remote bellows actuator 42 a puff of air pressure travels through air intake port 156 along air transport channel 152 out through the air exit port 62 and along tube 84 thus actuating a pneumatic switch which control roller valve 37 which is illustrated in FIG. 11 in a partial cross-section view.

The aspirate transport tube 24 extends from the rigid manifold handle 140 to aspirate collection-canister 28 which in turn is connected to a standard hospital-type wall-suction device 29. When the roller valve is open, a vacuum is instantaneously applied to the aspirate transport tube 24 by means of the standard hospital-type wall suction device 29. The vacuum within the aspirate transport tube 24 causes free blood-tinged fluid within the peritoneal cavity to be aspirated into the infusion-aspirator cannula 30, which is connected to the rigid handle 140 at the port 110. After passing through the port 110 of the rigid handle 140, the aspirate fluid is sucked through the aspirate fluid conduit 100 then through the aspirate channel 102 and finally through the aspirate transport tube 24 and into the aspirate collection canister 28.

Figure 12A:
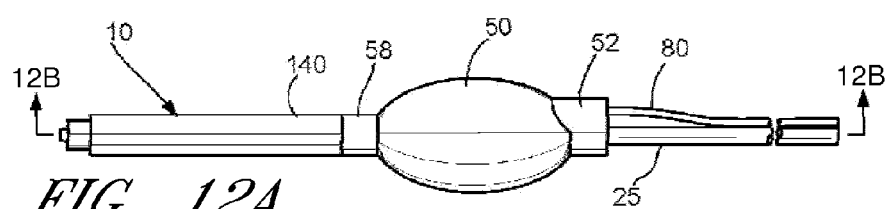
FIG. 12A shows a side elevational view of a remote actuator, illustrating an actuating tube, a fluid supply tube, a bellows, and a handle segment.
Figure 12B:
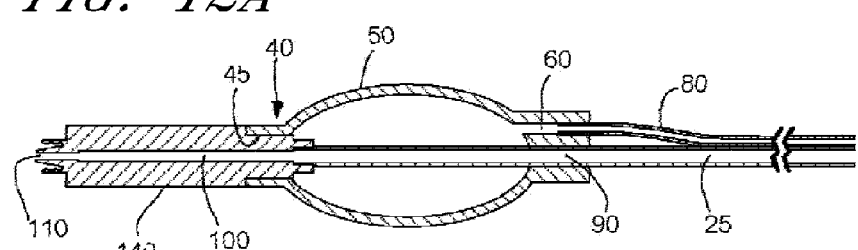
FIG. 12B shows a cross section diagram showing an actuating tube, a fluid supply tube, a bellows, and a handle segment, taken generally along lines 12B-12B of FIG. 12A.
Figure 12C:
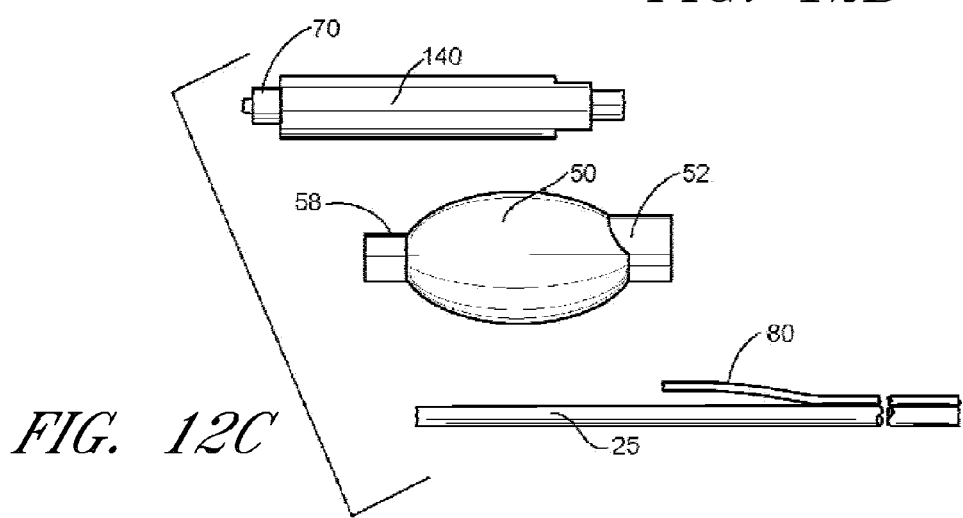
FIG. 12C shows an exploded view of an actuating tube, a fluid supply tube, a bellows, and a handle segment.

In another embodiment, illustrated in FIGS. 12A-12C, the remote actuator 10 further includes a sterile disposable sturdy medical device handle segment 140 securely affixed to an pneumatically sealed pouch 50 of a remote bellows actuator 40 and having a fluid outlet port 110, a fluid transport channel 100 and a fluid transport tube 25. This embodiment can be used for infiltration or infusion of therapeutic fluids in which case the actuating tube 80 connects to a pneumatic switch which actuates a peristaltic pump. In an alternate embodiment the device illustrated in FIG. 12A can be used as an aspiration device connected to an appropriate cannula for suctioning blood, tissue fragments or other fluids from a surgical site or as a liposuction handle.

Figure 13A:
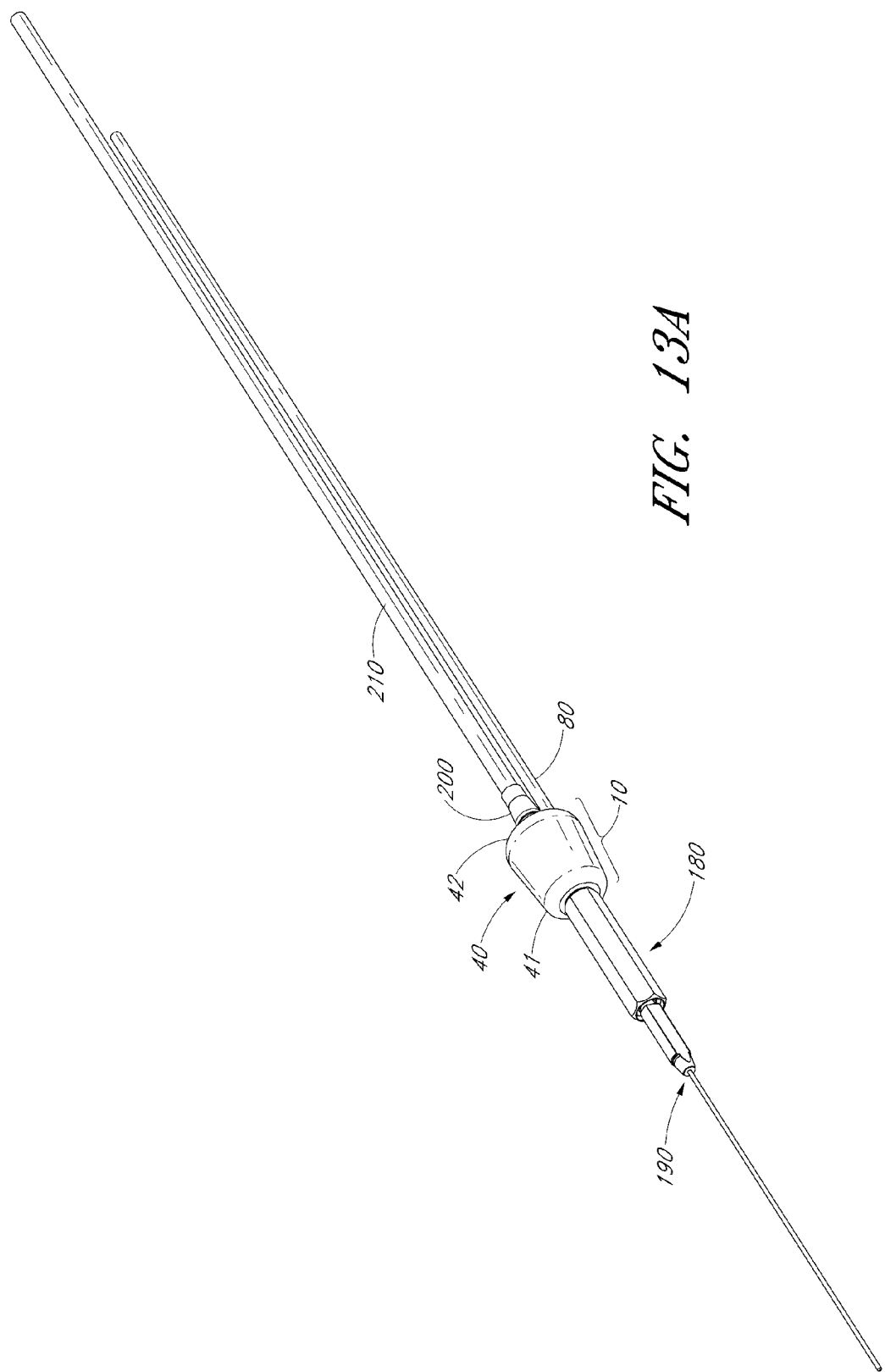
FIG. 13A shows a perspective view of an infiltration cannula assembly.
Figure 13B:
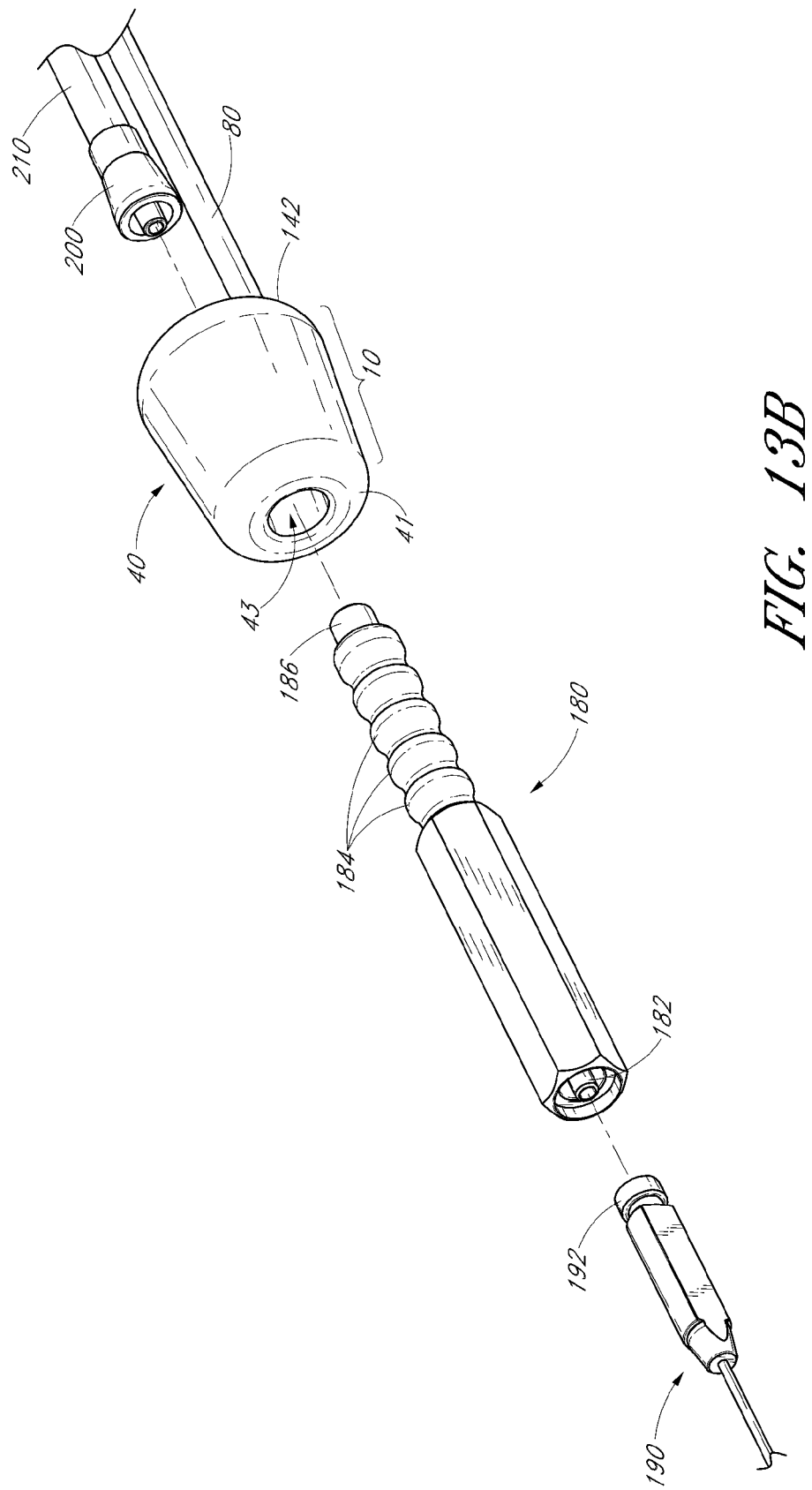
FIG. 13B shows an exploded view of an infiltration cannula assembly, illustrating an infiltration cannula, an infiltration handle, a remote actuator, a handle connector and an infiltration solution tube.
Figure 14B:
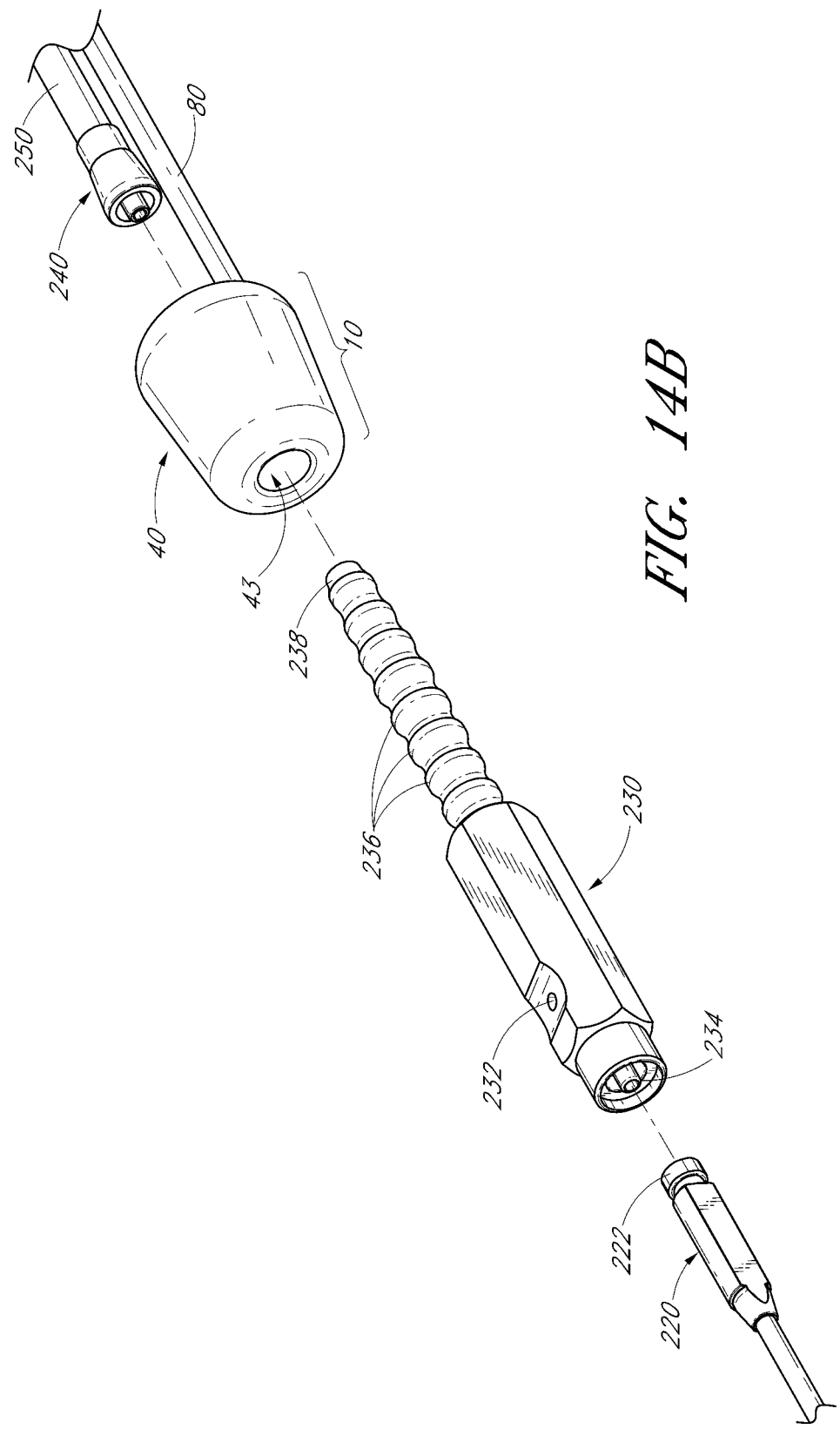
FIG. 14B shows an exploded view of an aspiration cannula assembly, illustrating an aspiration cannula, an aspiration handle, a remote actuator, a handle connector and an aspiration tube.

Some embodiments, e.g., as illustrated in FIGS. 13A-13D, relate to an infiltration cannula assembly provided with a remote actuator. In the illustrated embodiment, the treatment member is an infiltration cannula 190, which is reversibly attached to a handle 180. The handle 180 is further coupled to a bellows switch, or remote actuator 10. As shown in FIG. 13B, the infiltration cannula 190 has an integrated connector element, coupling member, or hub, 192, which is configured to couple to a receiving collar, 182, at the distal end of the handle 180, such that the lumen of the handle is fluidly coupled to the lumen of the cannula (not shown). The second, proximally disposed end region of the handle 180 has a plurality of ridges 184 and a proximal coupling member 186 for reversibly coupling to a connector 200 on the medical tube 210, which may be e.g., an infiltration solution tube 210. The handle 180 may be reusable or disposable. The connector 200 reversibly and fluidly couples the handle to e.g., the infiltration solution tube 210, which may be coupled to a solution reservoir and a peristaltic pump (not pictured). The central lumen of the remote actuator 10 is configured to slide over and securely engage the ridged end 184 of the handle 180. The remote actuator 10 may be either permanently or reversibly affixed to the handle. The remote actuator comprises a bellows 40 with a first end 41 and second end 42, a pneumatic port 60 (see FIG. 13C) provided on the second end and an actuating tube 80 which is pneumatically coupled to the inside region 44 of the bellows 40 through the pneumatic port. The actuating tube may be either permanently or reversibly affixed to the pneumatic port or the bellows, pneumatic port and actuating tube may be formed as a single unit. The bellows is configured such that a channel or lumen 43 runs from the first end to the second end through the center of the bellows, wherein the walls of the bellows create a pneumatically enclosed air pocket inside the bellows 40 and allowing the bellows to fit over and surround the handle. The inside region 44 (air pocket) is pneumatically sealed with the exception of an opening 62 at the port 60, where the lumen is pneumatically coupled to the actuating tube. The exterior wall of the bellows channel 43 may be provided with a series of ridges and valleys 46 that compliment the ridges and valleys 184 of the exteriorly-ridged segment of the handle 180, such that the ridges provided on the second end of the handle can be aligned with the valleys formed between two ridges in the exterior wall of the bellows channel. In some embodiments, friction between the exterior wall of the bellows channel and the exteriorly-ridged segment of the infiltration handle hold the remote actuator in place. In some embodiments (not illustrated), multiple bellows may be affixed in series on the infiltration handle. The length of the second end of the infiltration handle may be varied to accommodate multiple bellows.

In some embodiments, an infiltration cannula assembly may be sold as a unit or kit comprising an infiltration cannula, infiltration handle, bellows, and actuating tube or as individual components. In some embodiments the infiltration handle and bellows may be sold as a unit or kit optionally comprising an infiltration cannula and/or actuating tube.

Some embodiments, illustrated at FIGS. 14A-14D, relate to an aspiration cannula assembly provided with a remote actuator. An aspiration cannula 220 is reversibly attached by means of an integrated connector element, coupling member or hub, 222, to a first end 234 of an aspiration handle 230 such that the lumen 233 of the aspiration handle is coupled to the lumen of the aspiration cannula. A second end of the aspiration handle comprises an exteriorly-ridged segment 236 and a means for reversibly coupling 238 to a handle connector 240. The aspiration handle further comprises a channel 232 that communicates between the lumen of the aspiration handle and the handle surface. The aspiration handle 230 may be reusable or disposable. The handle connector 240 is configured to reversibly couple the aspiration handle to an aspiration tube 250, which may be coupled to a suction device, such as a vacuum pump or suction outlet (not pictured). A remote actuator 10 is provided on the second end 184 of the aspiration handle. The remote actuator may be either permanently or reversibly affixed to the aspiration handle. The remote actuator comprises a bellows 40 with a first end 41 and second end 42, a pneumatic port 60 provided on the second end and an actuating tube 80 which is pneumatically coupled to the bellows through the pneumatic port. The actuating tube may be either permanently or reversibly affixed to the pneumatic port or the bellows, pneumatic port and actuating tube may be formed as a single unit. The bellows is configured such that a channel 43 runs from the first end to the second end through the center of the bellows creating an enclosed lumen 44 and allowing the bellows to fit over and surround the aspiration handle. The lumen 44 is pneumatically sealed with the exception of an opening 62 at the pneumatic port 60, where the lumen is pneumatically coupled to the actuating tube. The exterior wall of the bellows channel 46 may be provided with a series of ridges and valleys that correspond to the ridges and valleys of the exteriorly-ridged segment of the aspiration handle 236, such that the ridges provided on the second end of the aspiration handle can be aligned with the valleys formed between two ridges in the exterior wall of the bellows channel. In some embodiments, friction between the exterior wall of the bellows channel and the exteriorly-ridged segment of the aspiration handle hold the remote actuator in place. In some embodiments (not illustrated), multiple bellows may be affixed in series on the aspiration handle. The length of the second end of the aspiration handle may be varied to accommodate multiple bellows.

In some embodiments the aspiration cannula assembly may be sold as a unit or kit comprising an aspiration cannula, aspiration handle, bellows, and actuating tube or as individual components. In some embodiments the aspiration handle and bellows may be sold as a unit or kit optionally comprising an aspiration cannula and/or actuating tube.

Figure 15B:
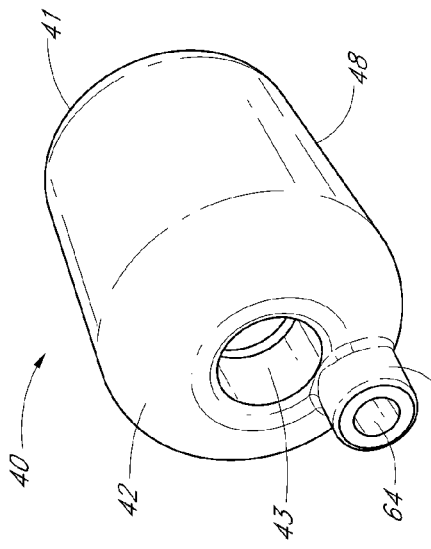
FIG. 15B shows a second-end perspective view of a bellows, showing a pneumatic port.
Figure 15D:
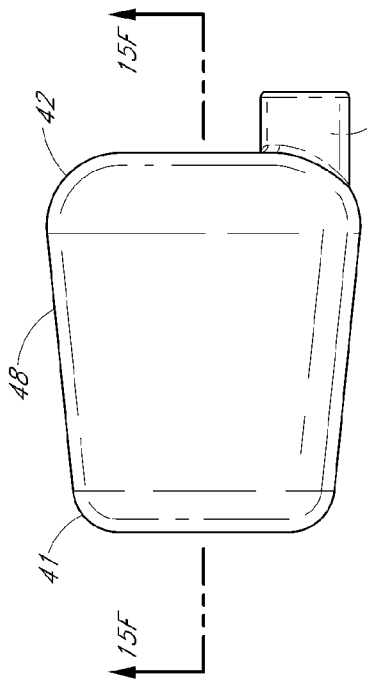
FIG. 15D shows a side elevational view of a bellows.
Figure 15A:
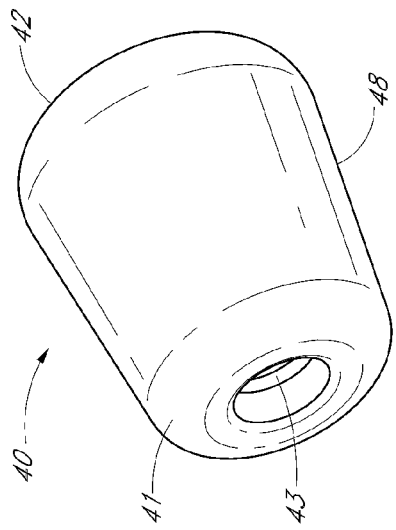
FIG. 15A shows a first-end perspective view of a bellows.
Figure 15C:
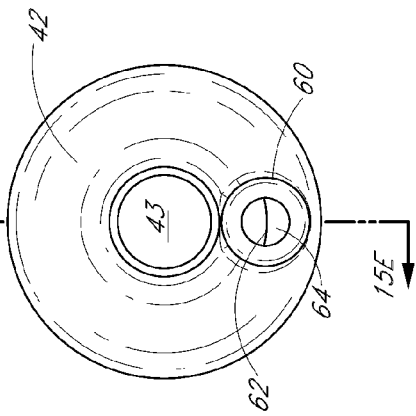
FIG. 15C shows a second-end elevational view of a bellows, showing a pneumatic port.

Some embodiments, illustrated at FIGS. 15A-14F, relate to a bellows for use in a remote actuator. The bellows comprises a first end 41 and a second end 48 which are connected by a surface wall 48 and a channel wall 46 and 47 to form a lumen 44 which is pneumatically sealed with the exception of an opening 62 at a pneumatic port 60 located on the second end. The pneumatic port is configured to pneumatically couple the lumen of the bellows to an actuating tube (not pictured). In the illustrated embodiments 13D, 14D and 15E, the channel wall is comprised of a series of alternating thicker 46 and thinner 47 areas, which form ridges and valleys. The ridges and valleys may be configured to complement a ridged segment of an aspiration handle, infiltration handle, or other treatment member. The diameter of the channel 43 can vary depending upon the diameter of the handle segment to which the bellows is affixed. The bellow walls 45 are preferably comprised of elastomeric materials that may be compressed by the user to create an air pressure pulse which is conducted by an actuating tube to a pneumatic switch of a medical device (not pictured). In the illustrated embodiment, the thicknesses of the first end wall 41, second end wall 42 and surface wall 48 are uniform. In other embodiments, the thicknesses of the walls may vary. In the illustrated embodiment, the bellows is configured such that diameter of the second end 42 exceeds the diameter of the first end 41 by a ratio of approximately 1.2 to 1.

While particular embodiments of the invention have been illustrated and described, it will be apparent that various modifications can be made without departing from the spirit and scope of the invention. For example, the pneumatically sealed pouch 50 or bellows 40 can take the form of a ball, ovoid, torroid, cone, hemisphere, or other shapes. Accordingly, it is not intended that the invention be limited, except as by the appended claims.

The teachings provided herein can be applied to other systems, not necessarily the system described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

These and other changes can be made to the invention in light of the above Detailed Description. While the above description details certain embodiments of the invention and describes the best mode contemplated, no matter how detailed the above appears in text, the invention can be practiced in many ways. Details of the system may vary considerably in its implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A remote actuator for a medical device that comprises a pneumatic switch, a medical tube and a treatment member, the remote actuator comprising:
    a bellows having a pneumatic port and an external coupling member disposed along an external surface of the bellows, the external coupling member being configured to reversibly attach the remote actuator to an external portion of the medical tube and/or treatment member, wherein the coupling member is configured so that the remote actuator can be attached to the medical tube and/or treatment member, detached from the medical tube and/or treatment member, and then reattached to the medical tube and/or treatment member; and
    an actuating conduit pneumatically coupled at a first end to the pneumatic port and configured to pneumatically couple at a second end to the pneumatic switch on the medical device, such that application of pressure to the bellows generates sufficient air pressure to actuate the pneumatic switch.

2. The remote actuator of claim 1, further comprising a handle portion.

3. The remote actuator of claim 1, wherein the bellows is pneumatically isolated from the medical tube and/or treatment member.

4. The remote actuator of claim 1, wherein the treatment member comprises a cannula for fluid infiltration, infusion or suction.

5. The remote actuator of claim 1, wherein at least the bellows of the remote actuator is sterile.

6. The remote actuator of claim 1, wherein the remote actuator is configured for a single use.

7. The remote actuator of claim 1, further comprising a salable package comprising an outer wrapper defining a sealed and sterile interior, wherein the remote actuator is located within said sealed and sterile interior.

8. The remote actuator of claim 1, wherein the actuating tube further comprising an optical fiber coupled to a light source, such that the bellows can be illuminated based on the status of the pneumatic switch.

* * * * *